(12) United States Patent
Schaefer, Jr.

(10) Patent No.: US 9,347,904 B1
(45) Date of Patent: May 24, 2016

(54) GRAIN-BIN MONITORING SYSTEM

(75) Inventor: Donald B. Schaefer, Jr., Blue Springs, MO (US)

(73) Assignee: C2Ag, LLC, Blue Spring, MO (US)

( * ) Notice: Subject to any disclaimer, the term of this patent is extended or adjusted under 35 U.S.C. 154(b) by 921 days.

(21) Appl. No.: 13/538,535

(22) Filed: Jun. 29, 2012

Related U.S. Application Data

(63) Continuation-in-part of application No. 12/391,906, filed on Feb. 24, 2009, now Pat. No. 8,806,772.

(51) Int. Cl.
*F26B 19/00* (2006.01)
*F26B 3/00* (2006.01)
*G01N 27/04* (2006.01)

(52) U.S. Cl.
CPC ............................ *G01N 27/048* (2013.01)

(58) Field of Classification Search
CPC ................................ F26B 19/05; F26B 9/063
USPC ......... 34/89, 491, 502; 73/431, 866.5, 76, 77; 439/415, 416, 427–431
See application file for complete search history.

(56) References Cited

U.S. PATENT DOCUMENTS

| | | | | |
|---|---|---|---|---|
| 2,135,937 A | * | 11/1938 | Gordon | 439/431 |
| 2,655,734 A | * | 10/1953 | Ohlheiser | 34/566 |
| 3,563,460 A | | 2/1971 | Nine | |
| 3,720,778 A | * | 3/1973 | Woertz et al. | 174/59 |
| 4,035,928 A | | 7/1977 | Sietmann et al. | |
| 4,121,135 A | * | 10/1978 | Hunt et al. | 439/66 |
| 4,152,840 A | | 5/1979 | Stille | |
| 4,293,854 A | | 10/1981 | Gookins et al. | |
| 4,522,335 A | | 6/1985 | Kallestad et al. | |
| 4,583,300 A | * | 4/1986 | Mast | 34/557 |
| 4,599,809 A | | 7/1986 | Parkes | |
| 4,688,332 A | | 8/1987 | Kallestad et al. | |
| 4,896,795 A | | 1/1990 | Ediger et al. | |
| 5,992,049 A | | 11/1999 | Trost | |
| 6,127,819 A | * | 10/2000 | Ouchi | 324/173 |
| 6,134,953 A | | 10/2000 | Verheecke | |
| 6,530,160 B1 | | 3/2003 | Gookins | |
| 6,747,461 B2 | | 6/2004 | Corak et al. | |
| 6,834,443 B2 | | 12/2004 | Bloemendaal | |

(Continued)

FOREIGN PATENT DOCUMENTS

KR 2003034829 A 12/2004

*Primary Examiner* — Kenneth Rinehart
*Assistant Examiner* — John McCormack
(74) *Attorney, Agent, or Firm* — Nathan S. Smith; McDermott Will & Emery LLP

(57) ABSTRACT

A grain-bin monitoring system for monitoring relative humidity and temperature is described. The system includes a cable assembly with a support cable and two pairs of communication wires suspended in a grain bin. A plurality of sensor assemblies is coupled along the cable. The sensor assemblies include a housing that protects a sensor device and enables exposure to air within the bin. The sensor device is in electrical communication with a control unit through fasteners for the housing piercing the cable assembly and contacting the communication wires. Electrically conductive, elastomeric pads are disposed between electrical contacts on the sensor device and the fasteners to eliminate galvanic corrosion therebetween. The cable assembly and sensor assemblies are configured to minimize drag forces applied by grain particulate flowing along the cable assemblies. And the sensor assemblies and/or the sensor devices therein are easily replaceable on the cable assembly while in service.

21 Claims, 13 Drawing Sheets

(56) References Cited

U.S. PATENT DOCUMENTS

| | | |
|---|---|---|
| 6,986,294 B2 | 1/2006 | Fromme et al. |
| 7,240,029 B2 | 7/2007 | Kallestad |
| 7,243,857 B2 | 7/2007 | Kallestad |
| 7,736,052 B2 * | 6/2010 | Shumaker et al. ............ 374/170 |
| 8,806,772 B1 | 8/2014 | Schaefer, Jr. |
| 2004/0031335 A1 | 2/2004 | Fromme et al. |
| 2005/0252380 A1 | 11/2005 | Gastaldi et al. |
| 2009/0262781 A1 | 10/2009 | Shumaker et al. |
| 2009/0304339 A1 * | 12/2009 | Ohtsuka et al. ............... 385/114 |
| 2010/0212396 A1 | 8/2010 | Zenisek |
| 2011/0176383 A1 * | 7/2011 | Jewell ............................ 367/16 |

\* cited by examiner

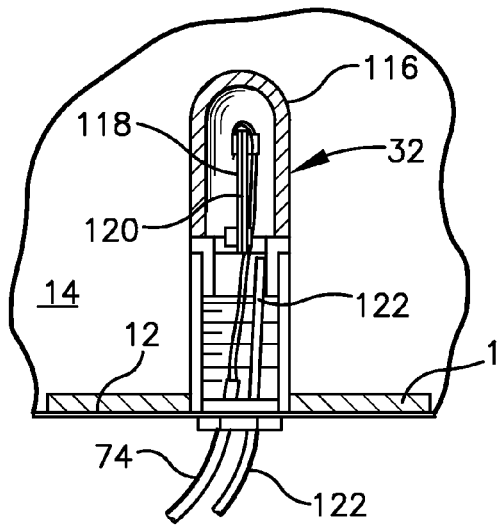
Fig. 11
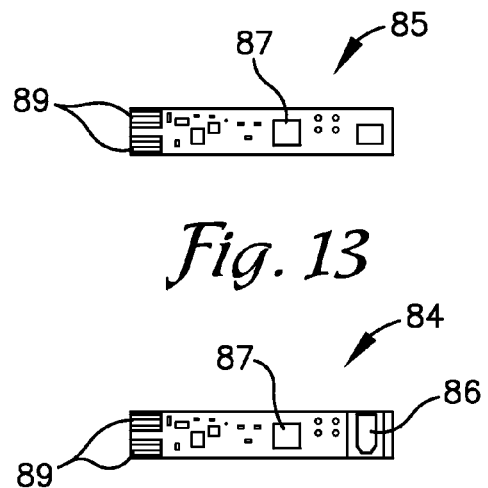
Fig. 13
Fig. 14
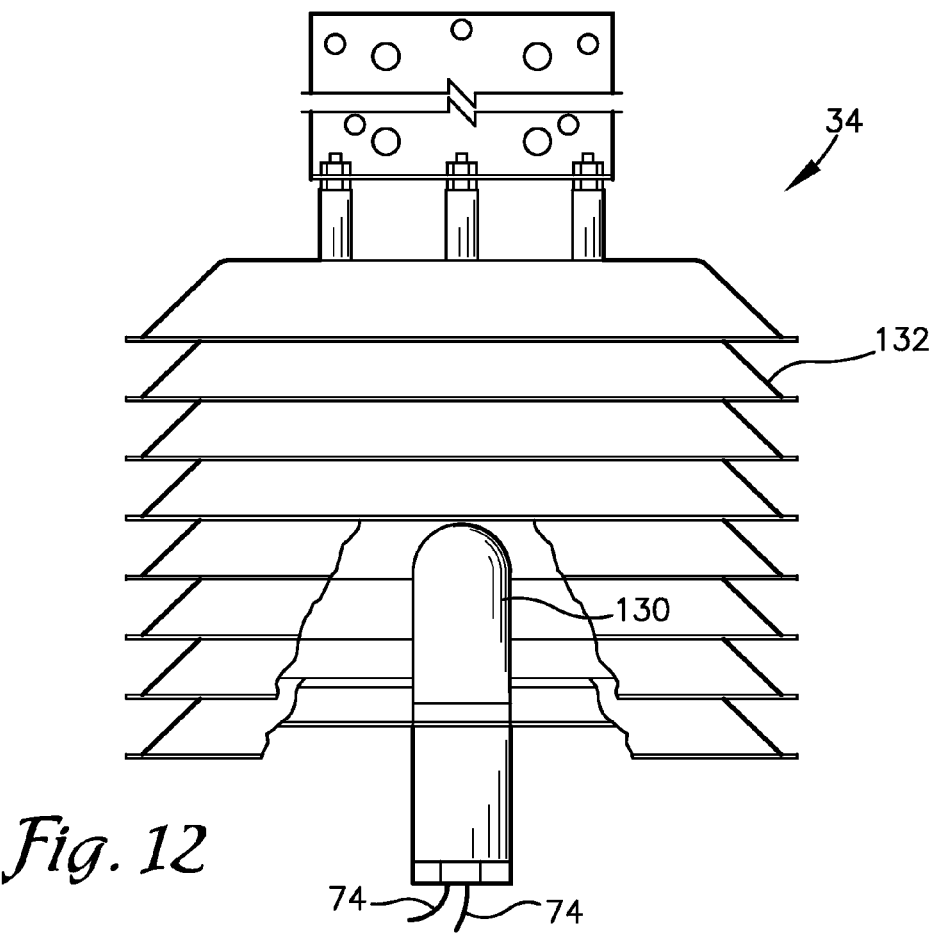
Fig. 12

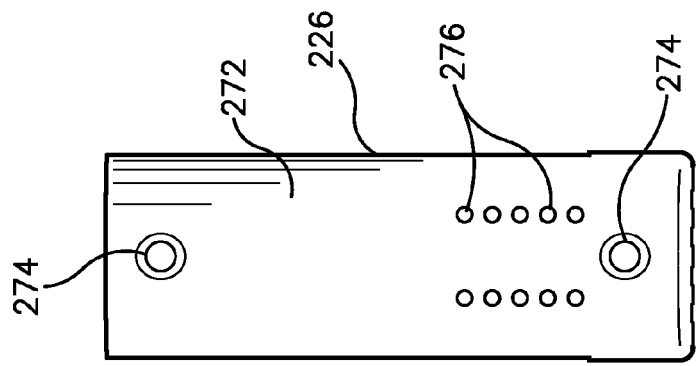
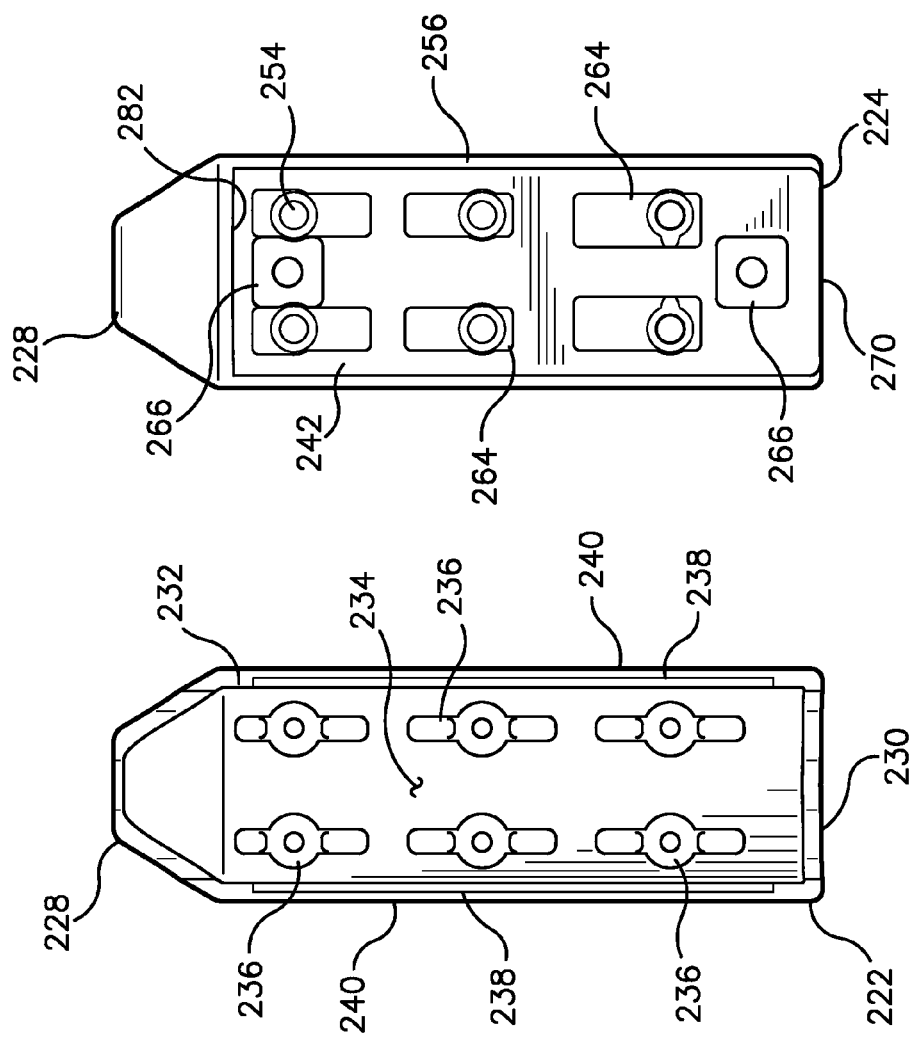

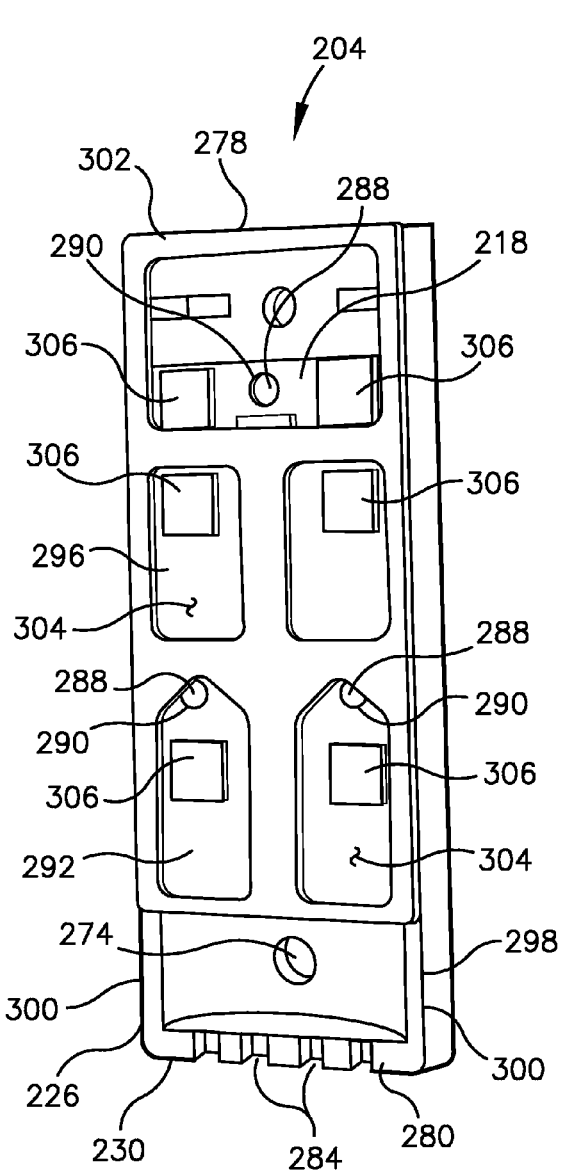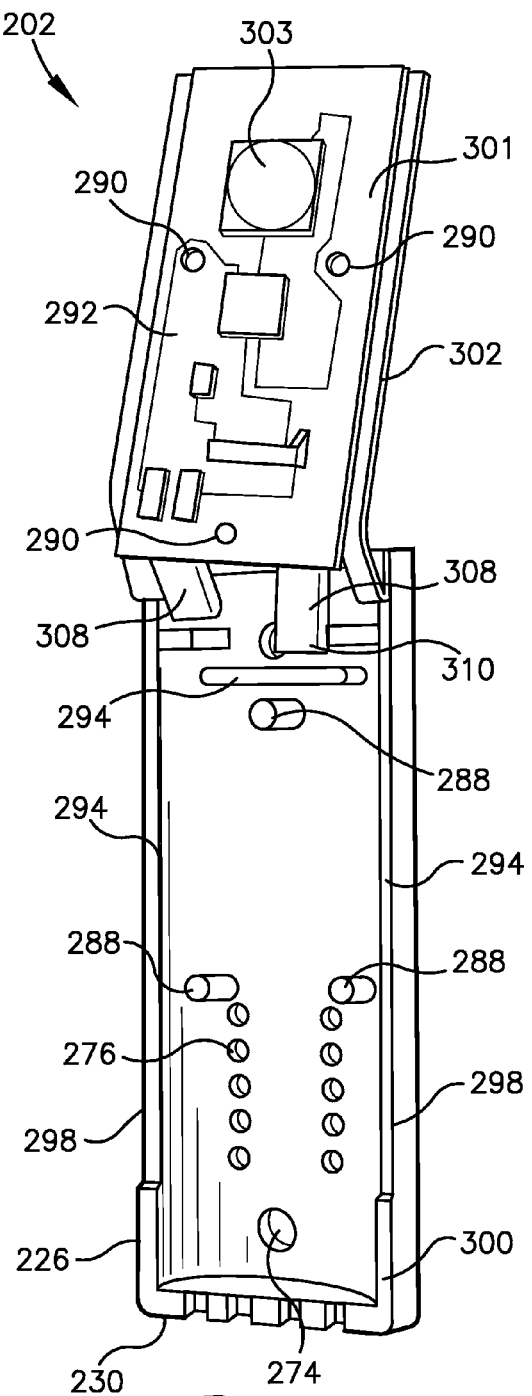
Fig. 23
Fig. 24

GRAIN-BIN MONITORING SYSTEM

CROSS-REFERENCE TO RELATED APPLICATIONS

This application is a continuation-in-part of and claims priority to U.S. patent application Ser. No. 12/391,906, filed Feb. 24, 2009 the disclosure of which is hereby incorporated herein in its entirety by reference.

BACKGROUND

An important need exists to dry grain quickly and effectively after harvest to retain maximum quality, to attain a moisture content sufficiently low to minimize infestation by insects and microorganisms (e.g., bacteria, fungi, etc.), to prevent germination and to maximize consumer acceptability of appearance and other organoleptic properties.

Grains are hydroscopic and will lose or gain moisture until equilibrium is reached with the surrounding air. Grain and air will exchange moisture until they reach their equilibrium moisture content (EMC). The EMC of air is dependent on the relative humidity and the temperature of the air, and this relationship, between EMC, relative humidity, and temperature, is different for each grain type (commodity). The relationship between EMC, relative humidity and temperature for many grains has been modeled by researchers: the results have been summarized in Brooker et al. (1974), Drying Cereal Grains, Westport: The Avi Publishing Company, Inc., 265 pp. For instance, EMC's for certain grains are shown in the chart immediately below.

| Grain | Relative Humidity (%) | | | | | | | |
|---|---|---|---|---|---|---|---|---|
| | 30 | 40 | 50 | 60 | 70 | 80 | 90 | 100 |
| | Equilibrium Moisture Content (% wb*) at 25° C. | | | | | | | |
| Barley | 8.5 | 9.7 | 10.8 | 12.1 | 13.5 | 15.8 | 19.5 | 26.8 |
| Shelled Maize | 8.3 | 9.8 | 11.2 | 12.9 | 14.0 | 15.6 | 19.6 | 23.8 |
| Paddy | 7.9 | 9.4 | 10.8 | 12.2 | 13.4 | 14.8 | 16.7 | — |
| Milled Rice | 9.0 | 10.3 | 11.5 | 12.6 | 12.8 | 15.4 | 18.1 | 23.6 |
| Sorghum | 8.6 | 9.8 | 11.0 | 12.0 | 13.8 | 15.8 | 18.8 | 21.9 |
| Wheat | 8.6 | 9.7 | 10.9 | 11.9 | 13.6 | 15.7 | 19.7 | 25.6 |

*wet basis
Source: Brooker et a. (1974)

There are two basic mechanisms involved in the drying process: the migration of moisture from the interior of an individual grain to the surface and the evaporation of moisture from the surface to the surrounding air. The rate of drying is determined by the moisture content and the temperature of the grain and the temperature, the relative humidity and the velocity of the air in contact with the grain. In general, higher airflow rates, higher air temperatures and lower relative humidities increase drying speed. The rate of moisture movement from high moisture grain to low relative humidity air is rapid. However, the moisture movement from wet grain to moist air may be very small or nonexistent. Also, higher airflow rates generally result in higher drying rates.

Traditionally, grain crops were harvested during a dry period or season and simple drying methods such as sun drying were used. However, maturity of the crop does not always coincide with a suitably dry period. Furthermore, the introduction of high-yielding varieties, irrigation, and improved farming practices has led to the need for alternative drying practices to cope with the increased production, and grain harvested during the wet season as a result of multi-cropping.

Among other techniques, in-line dryers have been used for drying the grain. However, these use high amounts of fuel and the dryers act like an oven and tend to cook out all of the moisture and over dry and crack the grain. As a result, it has become common for grain to be stored in bins and dried by mechanically moving air over and through the grain. This method is referred to as the "in-bin natural air drying" technique.

The in-bin natural air drying technique has several advantages. It can increase the quality of the harvested grain by reducing crop exposure to weather and reduce harvesting losses, including head shattering and cracked kernels. It also reduces the dependency on weather conditions for harvest and allows more time for post-harvest fieldwork.

However, current in-bin natural air drying systems have several disadvantages. Grains can only be stored without significant deterioration for a period of time depending on the storage conditions, primarily the grain's temperature and moisture content. Thus, an in-bin natural air drying system must quickly affect the temperature and moisture content to bring them within the range for long-term storage and thereafter maintain this state. But current systems do not include a method for measuring moisture of the grain while in the bin. They are thus not able to adjust settings based on actual measured data to dry the grain at the lowest energy costs and quickest timeframe. These systems also do not have individually replaceable sensors to allow inexpensive field repair and do not allow for remote access to the drying system via an Internet connection.

Additionally, drying fans are costly to operate: they should operate when the relative humidity level is low and temperature levels are generally warm. For instance, it is useless to run fans if it is raining Sensors for determining the condition of the grain placed throughout the bin help prevent hot spots. Also, it is preferable for the drying system to be centrally controlled, with remote access.

SUMMARY

Embodiments of the invention are defined by the claims below, not this summary. A high-level overview of various aspects of the invention are provided here for that reason, to provide an overview of the disclosure, and to introduce a selection of concepts that are further described in the Detailed-Description section below. This summary is not intended to identify key features or essential features of the claimed subject matter, nor is it intended to be used as an aid in isolation to determine the scope of the claimed subject matter. In brief, this disclosure describes, among other things, a grain bin monitoring system that includes integrated support and communications cables with modular temperature and relative humidity sensors coupled thereto.

In an embodiment, the improved grain drying system includes a master control unit external to the grain storage bin, which is preprogrammed with a desirable grain moisture content or EMC. Condition sensor assemblies mounted within the grain bin and extending into the mass of stored grain determine the moisture content and the temperature of the grain within the grain bin. Sensors mounted in the bin's plenum determine temperature, relative humidity and air pressure. A weather station mounted externally of the grain bin determines the outside air temperature and relative humidity. The master control unit selectively activates the grain bin's drying fan based on the temperature and relative humidity readings of the atmospheric air as measured by the weather station and the plenum sensors, and based on the temperature and moisture content as determined from the sensor assemblies within the grain bin. A radio or cellular modem allows for communication of the grain's condition to a user's personal computer or a remote data center.

The internal sensor assemblies are secured to flexible cables hung or suspended within the grain bin at different levels at which the sensor assemblies will be surrounded by grain stored in the bin. The cable supports the sensor assemblies and provides electrical communication between the sensor assemblies and an associated control unit. The sensor assemblies may be secured in a spaced relationship along the cable so that the grain condition can be determined throughout the grain bin. Each cable's sensor assemblies determine temperature, relative humidity, or both temperature and relative humidity of the grain throughout the bin. The use of multiple cables with multiple sensors aids in accurately determining the grain's condition throughout the bin.

Each of the cables comprises five separate parallel members that are encased in a casing of polyvinylchloride (PVC) or similar material. The casing maintains relative positions of the members and decreases friction between the cable and grain in the bin. A central member of the cable supports the cable against pulling forces applied by grain flowing into or out of the bin. Two pairs of communication members are disposed on opposite sides of the central member. The communication members of each pair are in close proximity but do not touch.

Each sensor assembly includes a sensor support which may be formed from a base and an intermediate portion that are secured to opposite sides of the cable by fasteners passing through the intermediate portion, through the cable between the communication members of each pair of communication members, and into the base. A cover is fastened to the intermediate portion and includes a sensor device comprising a printed circuit board with one or more of a temperature sensor and a relative humidity sensor affixed thereto. The sensor device is placed in electrical communication with the fasteners, which are also in electrical communication with each of the pairs of communication members in the cable. As such, temperature and/or relative humidity data collected by the sensor devices is communicated to the associated control unit via the pairs of communication members in the cable.

Various objects and advantages of this invention will become apparent from the following description taken in relation to the accompanying drawings wherein certain embodiments of this invention are set forth by way of illustration and example. The drawings constitute a part of this specification, include exemplary embodiments of the present invention, and illustrate various objects and features thereof.

DESCRIPTION OF THE DRAWINGS

Illustrative embodiments of the invention are described in detail below with reference to the attached drawing figures, and wherein:

FIG. 11 is a front sectional view of a plenum sensor of the grain drying system mounted in the grain bin in accordance with an embodiment of the invention;

FIG. 12 is a front view of a weather station of the grain drying system partially broken away to show the weather sensor therein in accordance with an embodiment of the invention;

FIG. 13 is a top view of a temperature sensor board of the grain drying system in accordance with an embodiment of the invention;

FIG. 14 is a top view of a moisture sensor board of the grain drying system in accordance with an embodiment of the invention;

FIG. 20 is a front plan view of a base of a sensor housing of one of the sensor assemblies depicted in accordance with an embodiment of the invention;

FIG. 21 is a front plan view of an intermediate portion of the sensor housing of the sensor assembly depicted in accordance with an embodiment of the invention;

FIG. 22 is a front plan view of a cover of the sensor housing of the sensor assembly depicted in accordance with an embodiment of the invention;

FIG. 23 is a rear perspective view of the cover with an electronic sensor formed on a circuit board connected thereto and showing a side of the circuit board including electrical contacts and a sealing gasket surrounding the contacts in accordance with an embodiment of the invention;

FIG. 24 is a view similar to FIG. 23 with the circuit board partially removed from the cover and shown flipped over to show an opposite side of the circuit board as shown in FIG. 23;

DETAILED DESCRIPTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
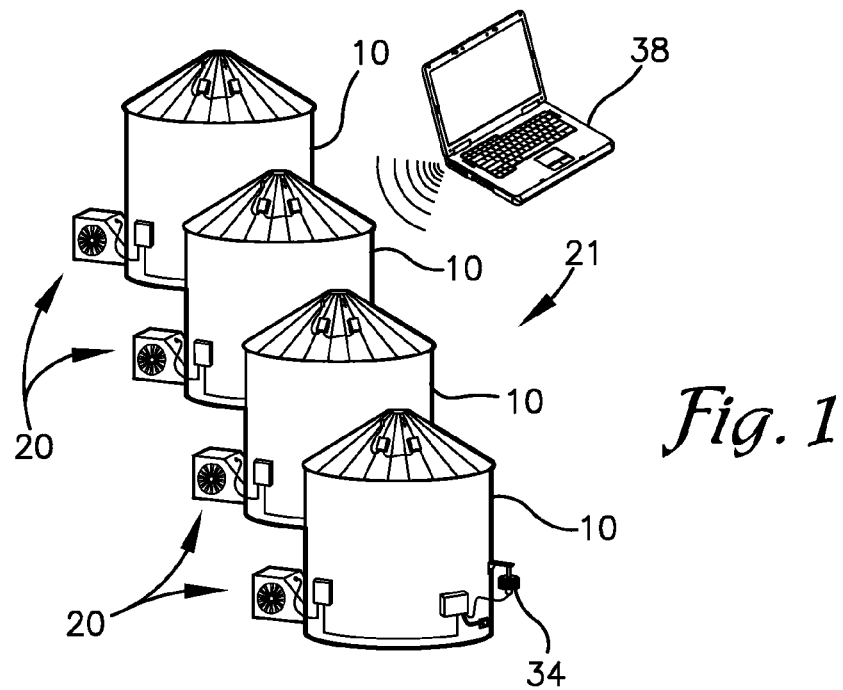
FIG. 1 is a perspective view of a cluster of grain storage bins interconnected in accordance with the grain drying system of the invention, with the remote, off-site communication shown diagrammatically in accordance with an embodiment of the invention.
Figure 2:
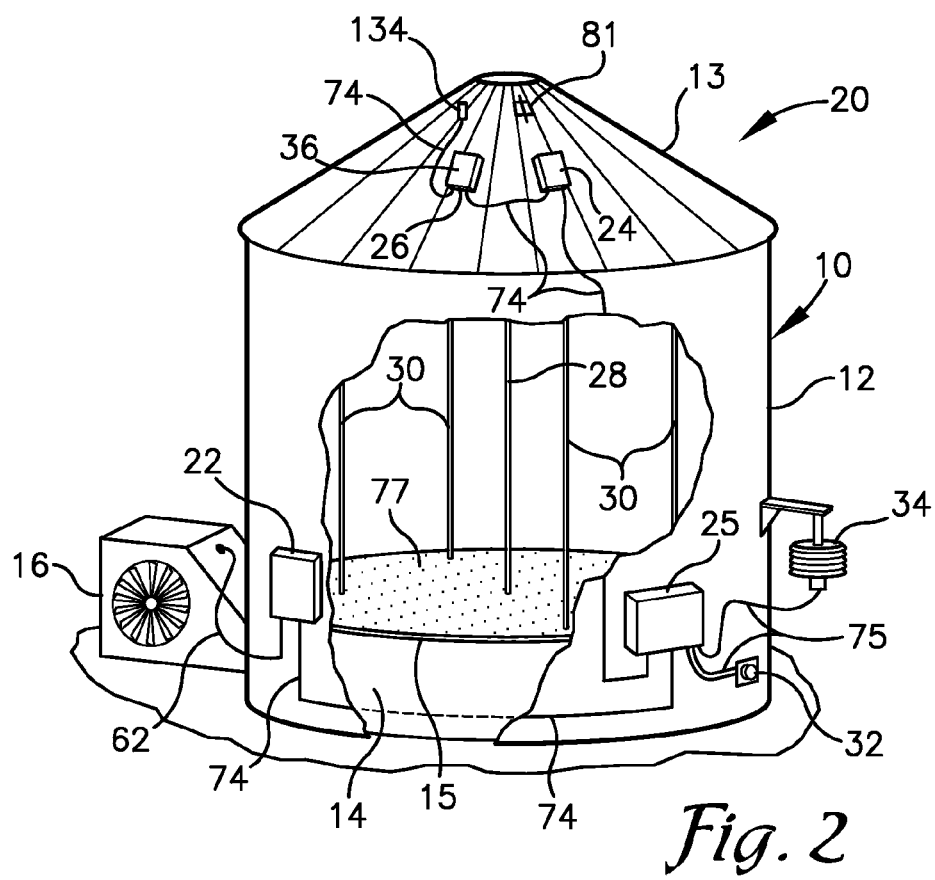
FIG. 2 is an enlarged, perspective view of one of the grain bins of FIG. 1, broken away to show the temperature and moisture cables of the grain drying system therein and with the grain removed for clarity.
Figure 3:
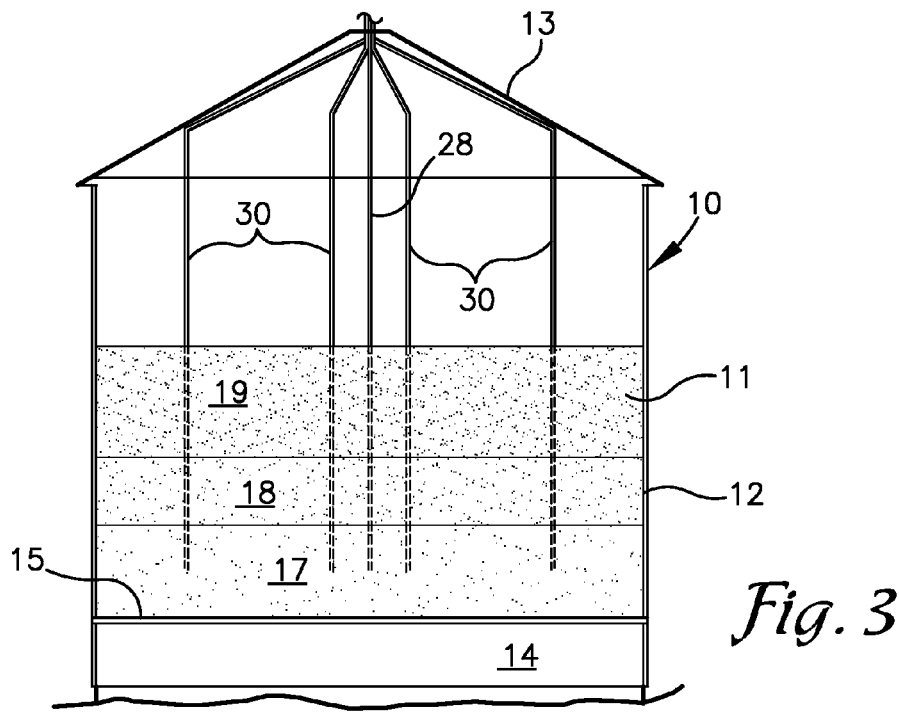
FIG. 3 is an enlarged, section of one of one of the grain bins of FIG. 1 with the components of the grain drying system external thereto removed for clarity, showing the cables and the grain stored therein.

Now, referring to the drawings and specifically FIGS. 1-3, conventional grain bins 10 for storing harvested grain 11 are shown which have been modified to include a grain drying control system 20 of the present invention. Each bin 10 has a side wall 12, a roof 13 and a plenum chamber 14 formed at the bottom of the bin 10, covered by a perforated floor 15. One or more fans 16 (and/or an optional heater(s), not shown) are installed outside each grain bin 10 adjacent the plenum chamber 14 to blow atmospheric or ambient air into the chamber 14 through the perforated floor 15 to dry or aerate the grain 11. As the grain 11 dries, it forms zones, represented diagrammatically by zones 17, 18 and 19 as shown in FIG. 3. The dry grain 17 extends upwardly from the floor 15, the wet grain 19 has been most recently harvested and is nearest to the top of the bin 10, and the drying grain 18 is sandwiched between the dry grain 17 and the wet grain 19.

Figure 7:
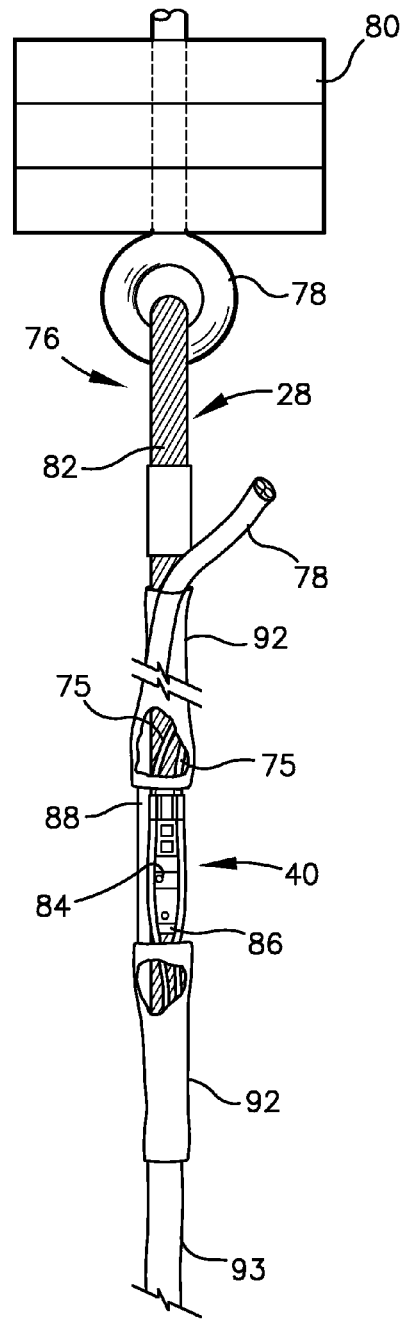
FIG. 7 is a fragmentary front plan view of a relative humidity cable of the grain drying system with portions broken away to show a relative humidity sensor and the cable construction in accordance with an embodiment of the invention.
Figure 10:
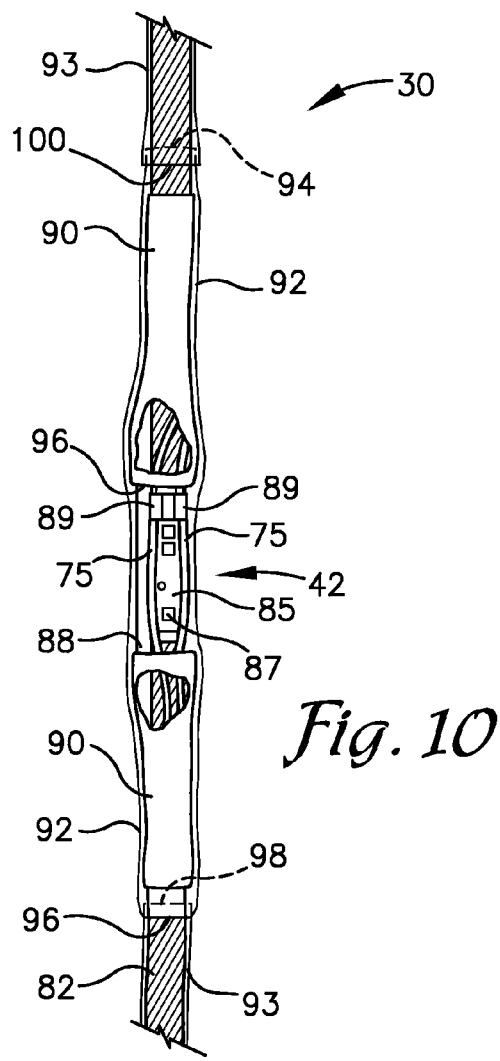
FIG. 10 is a fragmentary, front plan view of a temperature cable of the grain drying system with portions broken away to show a temperature sensor and cable construction in accordance with an embodiment of the invention.
Figure 15:
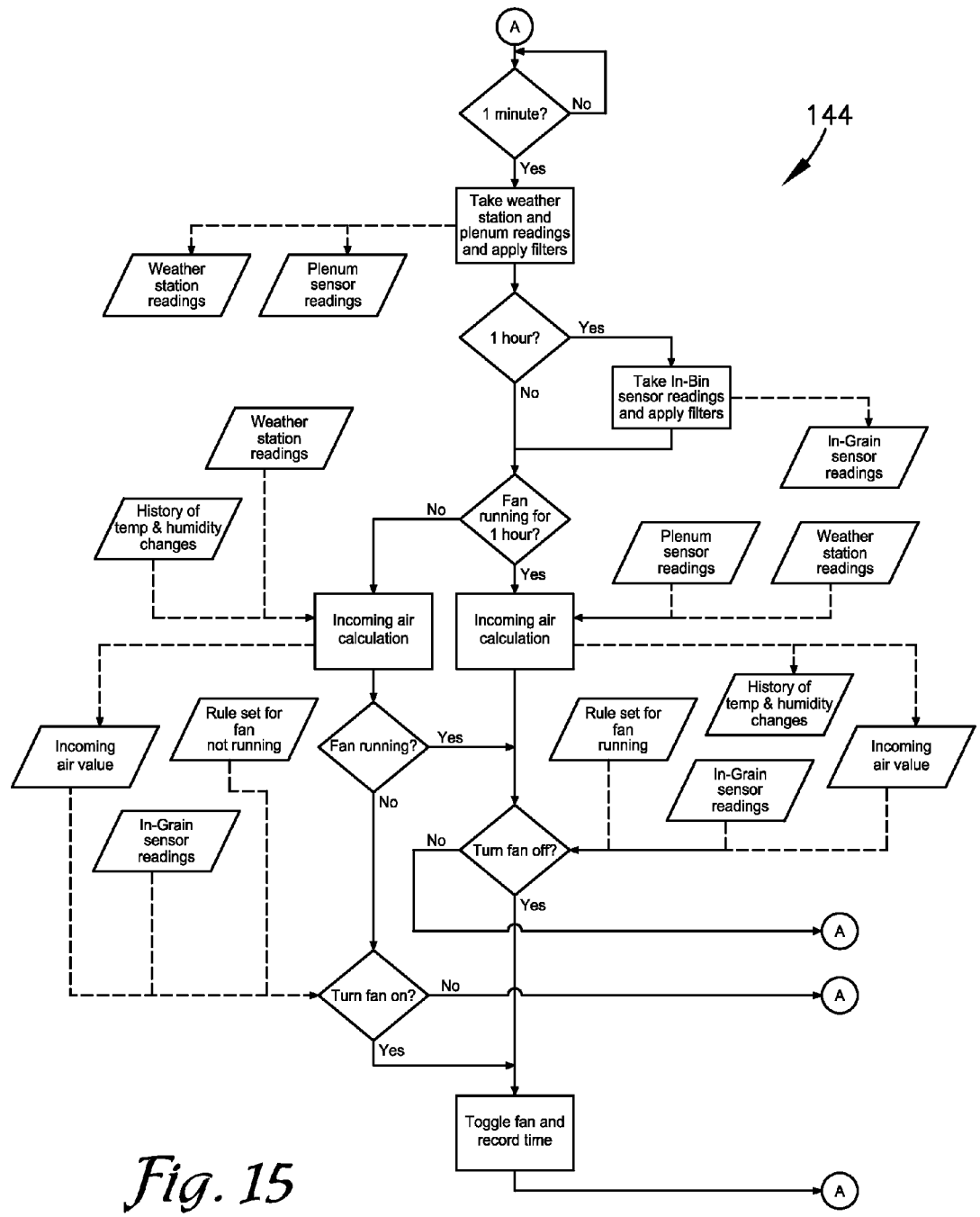
FIG. 15 is a flow chart showing fan control processing of the grain drying system in accordance with an embodiment of the invention.

As shown in FIGS. 1 and 2, the in-bin natural or atmospheric air grain drying system 20 of the present invention includes a master control unit 22, distributed control units 24, 25 and 26, a relative humidity sensor cable or cable assembly 28, temperature sensor cables or cable assemblies 30, a plenum condition sensor assembly 32, a weather station 34, a radio or cellular modem 36 and a remote user interface 38. Additionally, as shown in FIGS. 7 and 10, in-grain condition sensor assemblies 40 and 42 are secured along the respective cables 28 and 30. Sensor assemblies 40 determine the relative humidity and the temperature of the grain 11 by measuring the temperature and the relative humidity of the air surrounding the individual granules of grain within the stored mass. Sensor assemblies 42 determine the temperature of the grain 11 again by measuring the temperature of the air surrounding the grain within the stored mass. FIG. 1 shows a group of nearby bins 10, each with the drying system 20 installed thereon, forming a cluster 21 of bins 10.

Each distributed control unit 24, 25 and 26 communicates with the master control unit 22. Depending on the conditions detected by the sensor assemblies 32, 40, and 42 and the weather station 34 and communicated to the master control unit 22, the master control unit 22 selectively activates the drying fan 16 when it is efficient and effective to do so to achieve and maintain the grain's selected EMC based upon a comparison of the detected conditions relating to external temperature and humidity and the temperature and humidity within the mass of grain to be dried. The measured temperature and humidity within the plenum 14 may also be factors used to determine fan operation. Generally, if the external relative humidity is lower than the relative humidity within the mass of grain and the external temperature relatively high, the master control unit 22 will activate the fan 16. The system 20 dries the grain 11 throughout the grain bin 10 to its selected EMC quickly and efficiently to help prevent over-drying or other grain degradation and allows for communication between the system 20 and the user with regard to the grain's condition.

Figure 5:
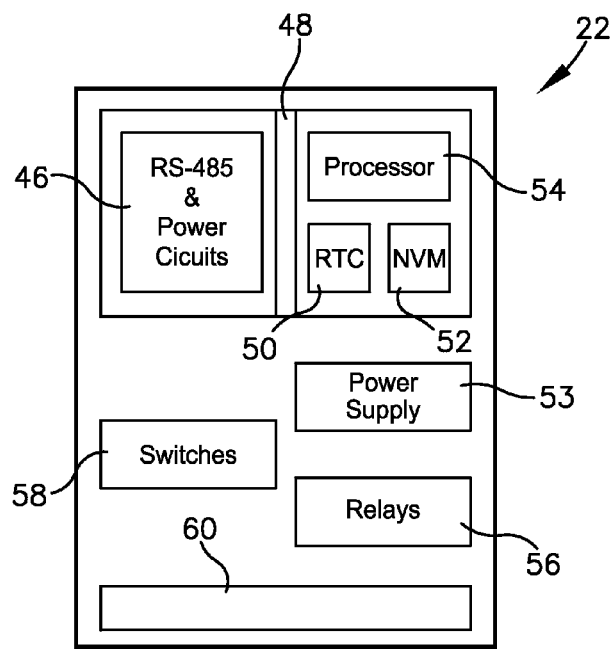
FIG. 5 is a front diagrammatic view of the master control unit of the grain drying system in accordance with an embodiment of the invention.

As shown in FIG. 2, the master control unit 22 is mounted on the exterior of the bin's sidewall 12 near the fan 16 and at an easily accessible height from the ground. As shown schematically in FIG. 5, the master control unit 22 includes power circuitry 46, isolation circuitry 48, a real-time-clock 50, non-volatile memory 52, a power supply 53, a microprocessor and firmware 54, relays 56, switches 58 and a terminal block 60. The memory 52 stores the grain type and corresponding selected or desired EMC among other information as well as the time and date during periods when the system's input power supply 53 is off. The microprocessor and firmware 54 run the software instructions required for the fan processing. The isolation circuitry 48 extends between the power circuitry 46 and the clock 50, the memory 52 and the processor 54 to prevent damage to the connected devices in the case of an electrical surge. The relays 56 and switches 58 automatically activate the fan 16 through a pair of wires 62 that run between the master control unit's terminal block 60 and the fan 16.

The distributed control unit 24 is mounted on the roof of the grain bin 10 near the ends of the humidity and temperature cable assemblies 28 and 30. It controls the sensor assemblies 40 and 42 on a plurality of cable assemblies 28 and 30 for determining the in-bin grain conditions. In an embodiment, up to eight cable assemblies 28, 30 are controlled by the distributed control unit 24. Distributed control unit 25 is mounted on the sidewall 12 of the grain bin 10 near the plenum sensor 32 for controlling the plenum sensor assembly 32 and the weather station 34 and for determining the out-of-grain environment condition. The distributed control unit 26 is preferably mounted on the roof 13 of the grain bin 10 near the radio/modem 36 and controls the local communication between bins 10 and the remote communication with the remote interface 38.

Figure 6:
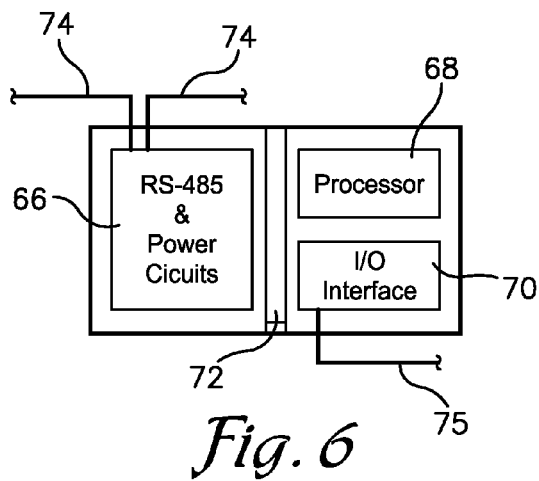
FIG. 6 is a front diagrammatic view of a distributed control unit of the grain drying system in accordance with an embodiment of the invention.

As shown schematically in FIG. 6, each distributed controller 24, 25, and 26 includes power circuitry 66, a microprocessor 68, an input/output interface with sensor or cell modem/radio circuitry 70, and isolation circuitry 72. Similar to the isolation circuitry 48 of the master control unit 22, the isolation circuitry 72 extends between the power circuitry 66, and the processor 68 and the I/O interface 70 to prevent damage to the connected devices in the case of an electrical surge. The distributed control units 24, 25, and 26 communicate with the master controller 22 via a pair of RS-485 communication wires 74 or other wired or wireless connection.

As seen in FIG. 2, the wire pair 74 preferably connects the master control unit 22 and each of the distributed control units 24, 25, and 26 together in a daisy chain. In an embodiment, the communication protocol parameters are: RS-485 for electrical signal levels; asynchronous 8-bit characters at 9600 baud with one start bit, one stop bit and no parity; and poll/response messaging where the master control unit 22 polls a specific distributed control unit 24, 25, or 26 for information and the distributed control unit 24, 25, or 26 sends a response. Each distributed control unit 24, 25, and 26 has an address assignment, so that each polling message contains an address field for the destination address, and each response contains an address field for the source address.

As seen in FIGS. 2 and 7, a wire pair 75 is secured along the cables 28 and 30 to communicate the grain conditions from the sensor assemblies 40 and 42 back to the controller 24.

Similarly, the wires 75 interconnect the plenum sensor assembly 32 and the weather station 34 with the controller 25.

The sensor cables 28 and 30 include an upper end 76 and a lower end 77. The upper end 76 of the cables 28 and 30 is secured to and hangs vertically from the roof of the grain bin 10 or from another structure (not shown) near the roof of the grain bin 10, e.g. a cross-member. The lower ends 77 of the cables 28 and 30 are spaced just above the perforated floor 15. The upper end 76 of each of the cables 28 and 30 is secured to, for example, an eyebolt 78. The eyebolt 78 is mounted through neoprene washers 80 and secured to the exterior side of the bin's roof 13 by a steel hanger 81 (only one shown in FIG. 2), however the upper ends 76 can be secured in other ways.

The cables 28 and 30 can be any desired length to fit within any grain bin 10. As shown, one relative humidity cable 28 hangs from near the center of the roof 13, with four temperature cables 30 spaced radially around the bin 10, between the relative humidity cable 28 and the sidewall 12 of the bin 10. However, any number of cables 28 and 30 can be used and mounted in any configuration, as desired.

Integrated Sensor Assemblies

In an embodiment of the invention, the sensor assemblies 40 and 42 are integrated into the cable assemblies 28 and 30. As seen in FIGS. 7-10, the cable assemblies 28 and 30 are similarly constructed in many respects. They each include the communication wires 75 mounted to extend along the length of a main support cable 82, with a group or string of sensor assemblies 40 or 42 secured in a spaced relationship along the wires 75 and the cable 82 as desired and depicted in FIG. 2. However, it is preferable for the sensor assemblies 40 and 42 to be spaced approximately four feet apart along the cable's length. The cable 82 is preferably formed of a flexible, galvanized steel cable to provide each sensor cable assembly 28 and 30 sufficient strength. This is especially important when the grain 11 is added or removed from within the bin 10, which places the cables 28 and 30 under tremendous strain due to the pull on the cables 28 and 30.

The cables 28 and 30 are wrapped in protective tubing 92 and 93. The protective tubing 92 covers the sensor assemblies 40 and 42 and each assembly's corresponding length of the wires 75 and the cable 82, and the protective tubing 93 covers the length of the wires 75 and the cable 82 between adjacent sensor assemblies 40 and 42. The tubing 92 and 93 is preferably polyvinyl chloride (PVC) shrink tubing, with tubing 92 having a ½" diameter and tubing 93 having a ⅜" diameter.

Each segment of the tubing 92 has an upper end 94 and a lower end 96. Similarly, each segment of the tubing 93 has an upper end 98 and a lower end 100. The cable assemblies 28 and 30 are preferably constructed from their lower end 77 to their upper end 76, with the upper ends 98 of the tubing segments 93 being overlapped by the lower ends 96 of the tubing segments 92 and the upper ends 94 of the tubing segments 92 being overlapped by the lower ends 100 of the tubing segments 93. This construction prevents any grain 12 from becoming lodged in the cables 28 and 30 as it is deposited or removed from the bin 10.

The sensor assemblies 40 and 42 do differ from one another. The sensor assemblies 40 are mounted along the relative humidity cable 28 and include a sensor circuit board 84 having both a relative humidity (or moisture level) sensor 86 and a temperature sensor 87 thereon, whereas the sensor assemblies 42 are mounted along the temperature cables 30 and include a sensor circuit board 85 having a temperature sensor 87 thereon but no relative humidity sensor 86. The circuit boards 84 and 85 are shown in FIGS. 14 and 13 respectively. Up to thirty sensors 86 and 87 can be attached to the same cable assembly 28 or 30. Thus, as shown in FIG. 2, the center relative humidity cable 28 detects moisture and moisture differences between vertical layers of the grain 11 in the bin 10, and all of the cables 28 and 30 detect temperature and are useful in finding hot spots or areas in which the grain 11 may be undergoing a chemical change or degradation.

Figure 8:
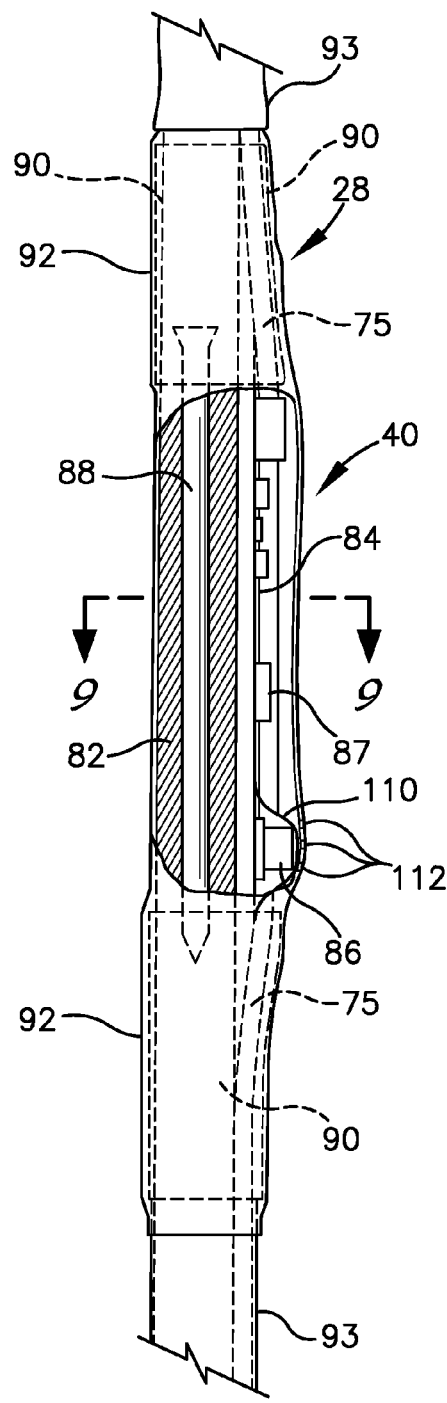
FIG. 8 is an enlarged, fragmentary side view of the relative humidity cable of FIG. 7, with portions broken away to show a relative humidity sensor.

Referring to FIG. 8, each relative humidity sensor 86 is covered with a mesh filter 110. The filter 110 overlays the sensor 86. The filter 110 helps prevent dust or grain particulate from damaging the sensor 86 and is preferably a very thin, fine polypropylene mesh material.

Figure 9:
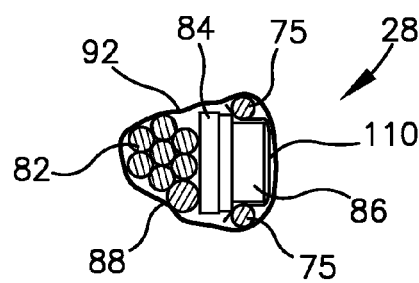
FIG. 9 is a cross-sectional view taken at detail 9-9 of FIG. 8, with the humidity sensor board shown.

Each sensor assembly 40 and 42 overlays a steel rod or nail 88 secured in place by two pieces of shrink tubing 90. As best seen in FIG. 9, the sensor circuit boards 84 or 85 lay over the steel cable 82 and the rod 88, which provide parallel supports for the circuit board 84 or 85. The combined diameters of the cable 82 and the rod 88 are preferably substantially equal to the width of the circuit boards 84 or 85. The wires 75 are secured by crimping them to the circuit boards 84 and 85 with fasteners 89. This also aids in securing the circuit boards 84 and 85 in place. With the relative humidity sensor assembly 40, the wires 75 lie along opposite sides of the relative humidity sensor 86 and over the mesh filter 110, thereby securing the mesh filter 110 in place and providing protection to the sensor 86.

The rod 88 is preferably steel and three inches in length. It lies along and parallel to the cable 82 below the circuit board 84 or 85 and thereby provides rigidity to the cable assembly 28 or 30 where the sensor circuit board 84 or 85 lays so that the board 84 or 85 bears little, if any, shear force when the sensor cable assembly 28 or 30 is moved or rolled prior to installation or when jarred by grain 11 as the bin 10 is filled or emptied. Although nails are readily available, any rigid rod-like member may be substituted or utilized.

The tubing pieces 90 secure the wires 75 and each end of the rod 88 to the cable 82 adjacent the ends of the sensor circuit board 84 or 85, sandwiching the circuit boards 84 or 85 therebetween. Polyolefin shrink tubing is preferred because it has an integral adhesive that melts into the braiding of the steel cable 82 to secure and affix the wires 75, the cable 82 and the rod 88 together.

The shrink tubing 92 secures the circuit boards 84 or 85 to the cable 82. The tubing 92 extends around the cable 82, the circuit board 84 or 85, the wires 75, the rod 88 and the polyolefin shrink tubing 90 to secure these elements together and provide abrasion resistance. As best seen in FIG. 8, with the relative humidity sensor assembly 40, the tubing 92 has apertures 112 therethrough. These apertures 112 are aligned over the relative humidity sensor 86 to allow air and moisture to exchange and equalize through the mesh filter 110 and the apertures 112, between the sensor 86 and the grain 11. As shown in FIG. 8, the tubing 92 includes three small apertures 112; however, the number of apertures may be varied.

Modular Sensor Assemblies

Figure 16:
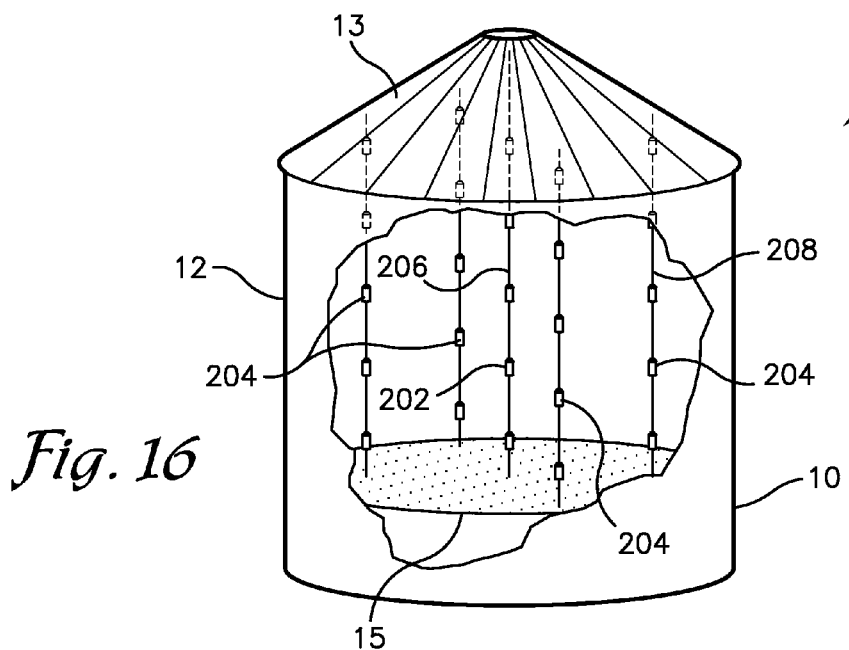
FIG. 16 is a diagrammatic view showing an alternative embodiment of sensor assemblies mounted on cable assemblies within a grain bin for sensing conditions therein in accordance with an embodiment of the invention.
Figure 17:
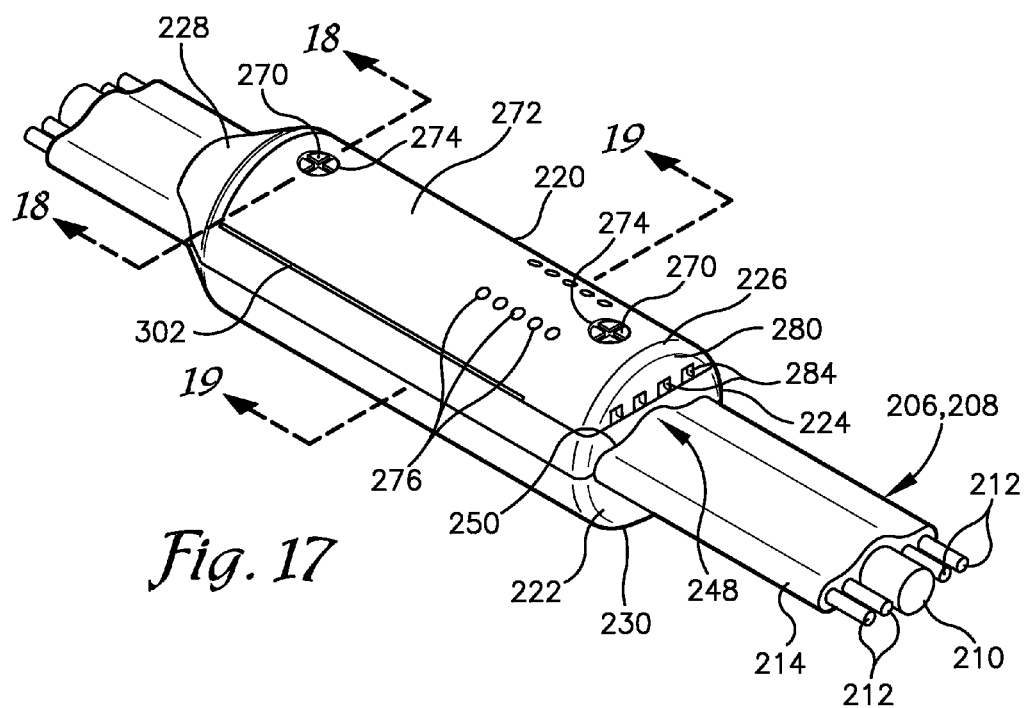
FIG. 17 is a fragmentary perspective view of a sensor assembly mounted on a cable assembly depicted in accordance with an embodiment of the invention.
Figure 18:
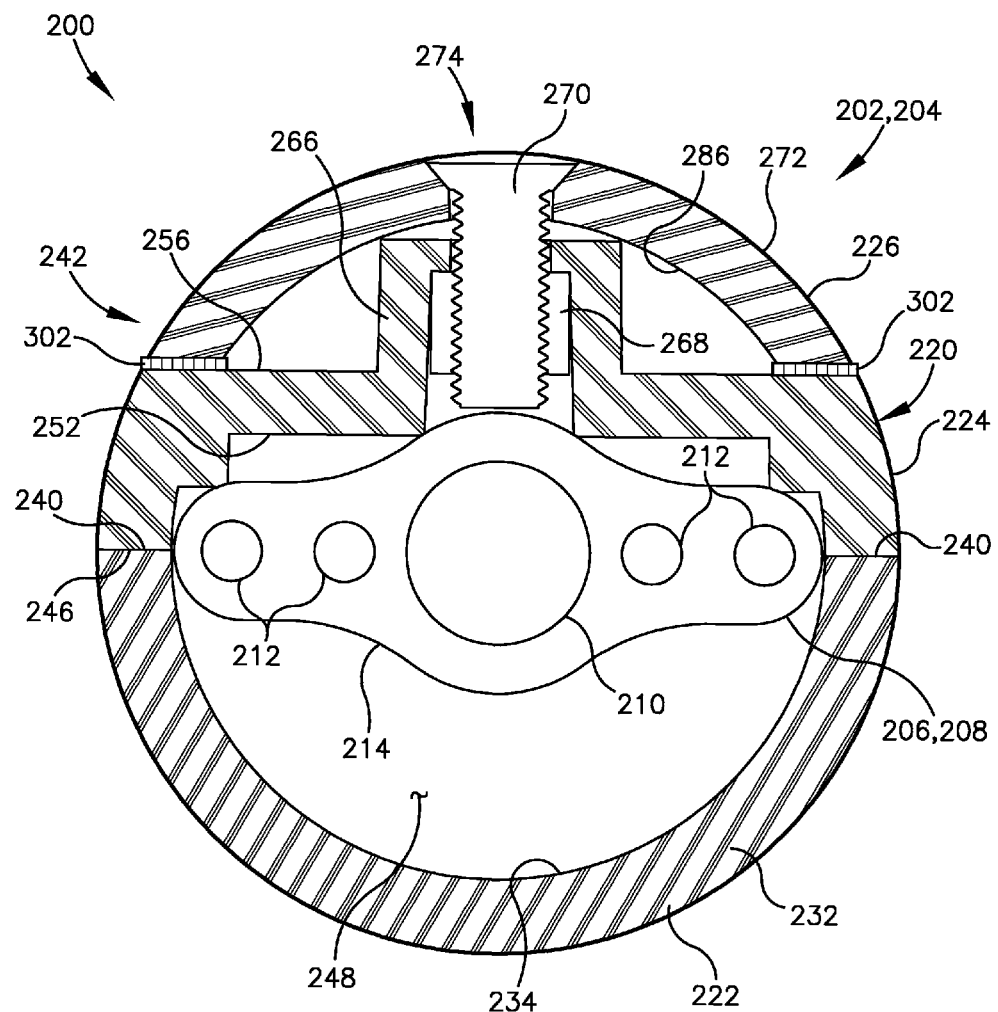
FIG. 18 is an enlarged cross-sectional view taken along line 18-18 of FIG. 17.
Figure 19:
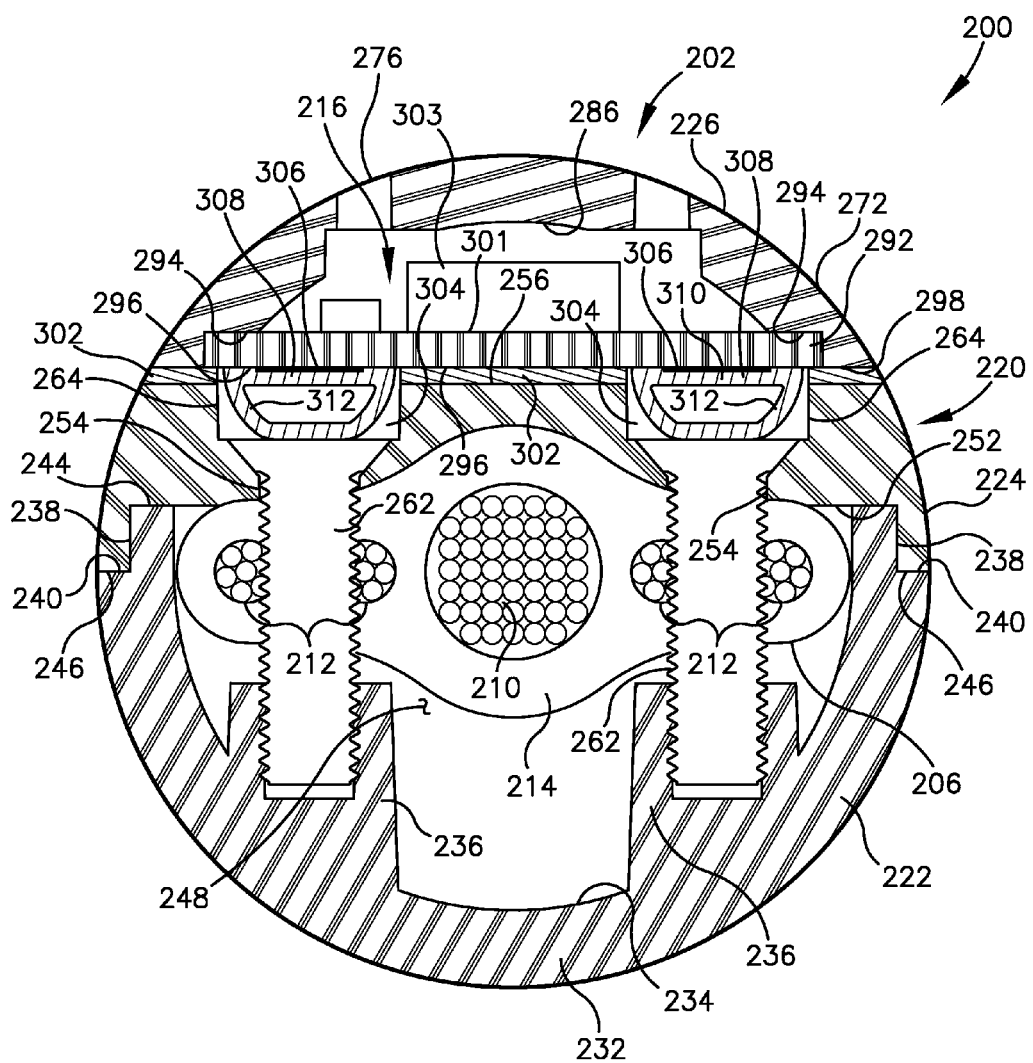
FIG. 19 is an enlarged cross-sectional view taken along line 19-19 of FIG. 17.

With reference now to FIGS. 16-26, in another embodiment, a grain-bin monitoring system 200 comprises a plurality of modular sensor units or assemblies 202 and 204 mounted on cable assemblies 206 and 208 respectively, as shown diagrammatically in FIG. 16. As best seen in FIGS. 17-19, the cable assemblies 206, 208 include at least a support member or cable 210 and two communication members, conductors, or wires 212 or, more preferably, a support cable 210 and two pairs of communication wires or conductors 212. Each of the pairs of communication wires 212 are disposed along an opposite side of the support cable 210 in a common plane and spaced apart from the support cable 210. In addition, the communication wires 212 in each pair are spaced apart from one another. As such, the cable assemblies 206, 208 have a non-circular cross-sectional shape or profile as depicted in FIG. 18. Both of the communication wires 212 of a single pair are electrically coupled to the same terminal on the distributed control unit 24, e.g. both wires 212 of one pair are connected to a positive terminal of the control unit 24 while both wires 212 of the second pair are connected to a negative terminal. The pairs of wires 212 thus each include a redundant wire 212.

The support cable 210 comprises any suitable cable, such as the cable 82, and may comprise a galvanized steel cable such as that known in the art as aircraft cable. In one embodiment, the support cable 210 comprises a braided galvanized steel cable having a 7×19 configuration, e.g. the cable is comprised of seven smaller cables that are braided together and each of the seven smaller cables includes nineteen strands therein. The support cable 210 has a diameter of approximately $3/16$ths inches (about 4.76 millimeters) and can withstand tensile loads of at least 5000 pounds. But properties of the cable 210 can be configured per application.

The communication wires 212 comprise braided, galvanized steel cables that are approximately $3/64$ths inches (about 1.19 millimeters) in diameter but can employ any suitable materials, dimensions, properties, and configurations, such as the communication wires 75. In an embodiment, the communication wires 212 comprise cables with a 7×7 configuration in which the cable is formed from seven smaller cables that are each comprised of seven strands.

A casing 214 is provided around the support cable 210 and the communication wires 212. The casing 214 provides a continuous solid enclosure around the support cable 210 and the communication wires 212 and maintains the relative positions of the support cable 210 and communication wires 212 in the coplanar and spaced apart orientation. The casing 214 preferably comprises a flexible material, such as a polyvinyl-chloride (PVC), plastic, nylon, or similar material that is extruded, pultruded, or otherwise formed around the support cable 210 and communication wires 212. Formation of the casing 214, such as by extrusion, may employ a die that maintains the positions of the support cable 210 and communication wires 212 while the casing 214 is extruded therearound. It is foreseen that the cable casing 214 could be formed relatively rigid or that the casing only encloses the communication wires but not the support cable 210. It is also foreseen that the cable assemblies 206 and 208 could be formed without the support cable 210 wherein the communication wires 212 might then be sized larger to resist damage due to the loads acting on or tugging downward on the cable as the grain 11 is drawn out of the grain bin 10 from the bottom.

The casing 214 is preferably sufficiently flexible to enable coiling of the cable assembly 206, 208 for shipment and to enable the cable assembly 206, 208 to assume a substantially linear profile when suspended from one end, such as in the grain bin 10. The casing 214 also has an exterior surface that has sufficient hardness to resist indentation, scaring, gouging, or the like caused by particles of grain being pressed against the surface or flowing along the surface. And the exterior surface is sufficiently smooth to minimize friction between grain particles flowing along the surface and to thereby minimize the load applied to the cable assembly 206, 208.

The modular sensor assemblies 202 and 204 are identical but for a sensor device 216 or 218 disposed therein. The sensor devices 216 and 218 shown may also be referred to as electronic sensors 216 and 218. The sensor device 216 is configured to detect relative humidity and temperature while the sensor device 218 is configured to detect only temperature. The sensor devices 216 and 218 may be the same as sensor devices employed in the sensor assemblies 40 and 42 respectively including a plurality of selected electronic components mounted on a circuit board, which is typically made of a somewhat brittle material such as glass or polymer fibers bonded together with an epoxy or the like. It is to be understood that other sensor technologies might be employed to detect other environmental characteristics or combinations thereof within the grain bin 10, such as, for example and not limitation, a sensor that senses relative humidity only, or one that detects carbon dioxide levels, among others. Such sensors and sensor technologies are within the scope of embodiments of the invention.

With further reference to FIGS. 20-22, the modular sensor assemblies 202, 204 shown comprise a three-part housing 220 that includes a base 222, an intermediate portion 224, and a cover 226. The base 222 and the intermediate portion 224 may be collectively referred to as a sensor support or sensor support assembly. The components 222, 224, 226 of the housing 220 of a preferred embodiment are formed from an injection molded, polypropylene plastic material that provides a smooth, low friction exterior surface that resists buildup of electrostatic charge. However, any suitable material and method of manufacture can be employed in embodiments of the invention. The housing 220 is also configured to withstand at least a minimum load, e.g. about 200 pounds, that might be applied by grain 11 in the bin 10 passing along the surface thereof. It is understood that various configurations of the housing 220 comprising a different number or type of components might be employed to perform the functions described herein—such configurations are within the scope of embodiments of the invention.

The sensor housing 220 has a substantially cylindrical form with a frustro-conical or pointed, leading or upper end 228 which narrows or converges inward and upward and a blunt, trailing or lower end 230. The housing 220 is divided lengthwise into the base 222 and the intermediate portion 224. As such, the base 222 comprises a wall 232 that forms half of the cylindrical form and leading and trailing ends thereof 228, 230. An interior surface 234 of the base 222 includes a plurality of reinforced bosses 236 extending therefrom. The wall 232 of the base 222 has an interior diameter that is larger than that of the cable assembly 206, 208 to which the base 222 is coupled. A flange 238 extends (upwards as viewed in FIG. 19, but sideways in use) from opposite edges 240 of the wall 232 a distance along the length of the base 222.

The intermediate portion 224 forms an opposite half of the cylindrical form and leading and trailing ends 228, 230 of the housing 220 but includes a recessed section 242 over which the cover 226 couples to complete the cylindrical form of the housing 220. Recesses 244 along edges 246 of the intermediate portion 224 accept the flanges 238 on the base 222 and enclose the cable assembly 206, 208 therebetween.

Figure 25:
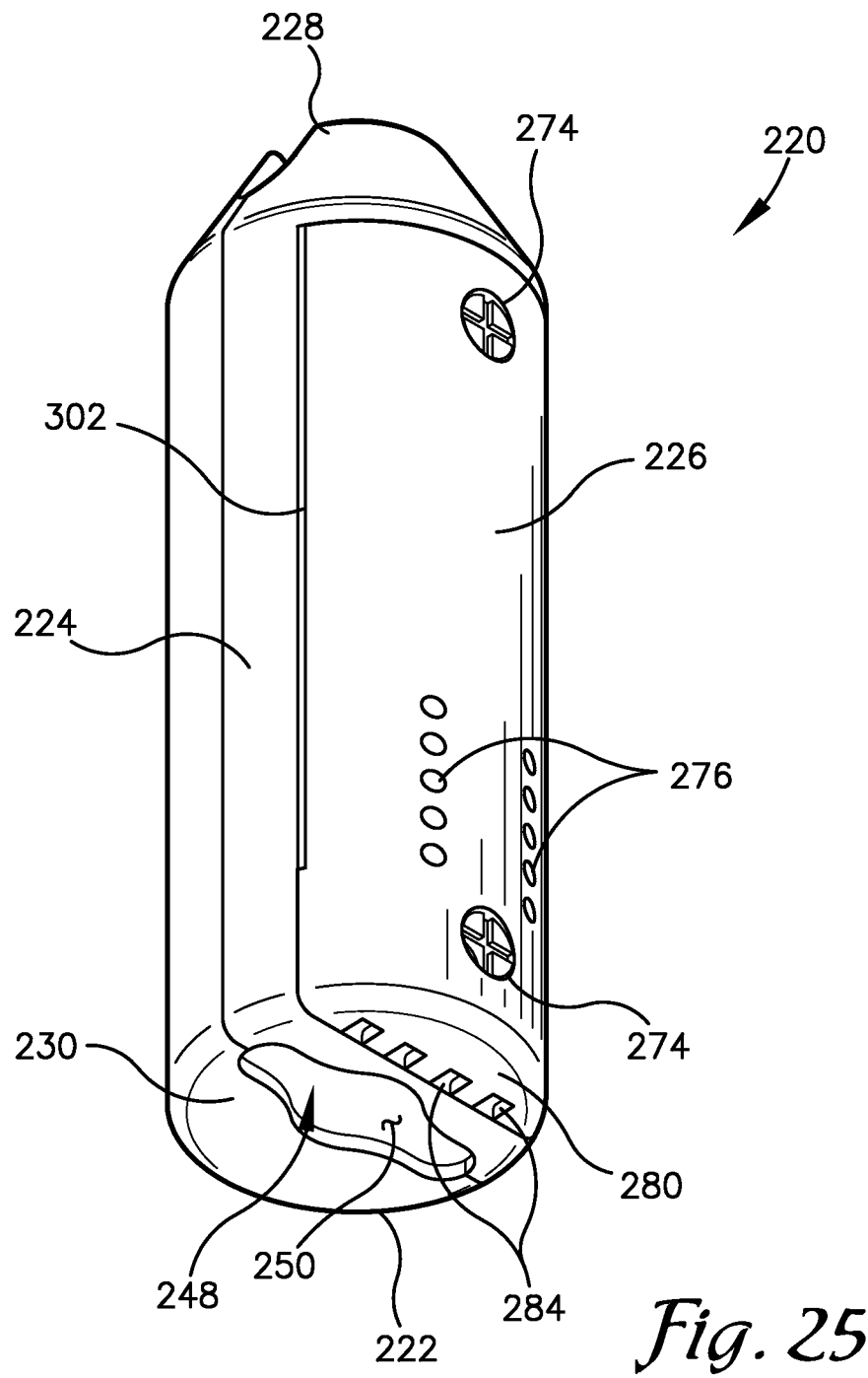
FIG. 25 is a bottom perspective view of an assembled sensor assembly separated from a cable assembly depicted in accordance with an embodiment of the invention.
Figure 26:
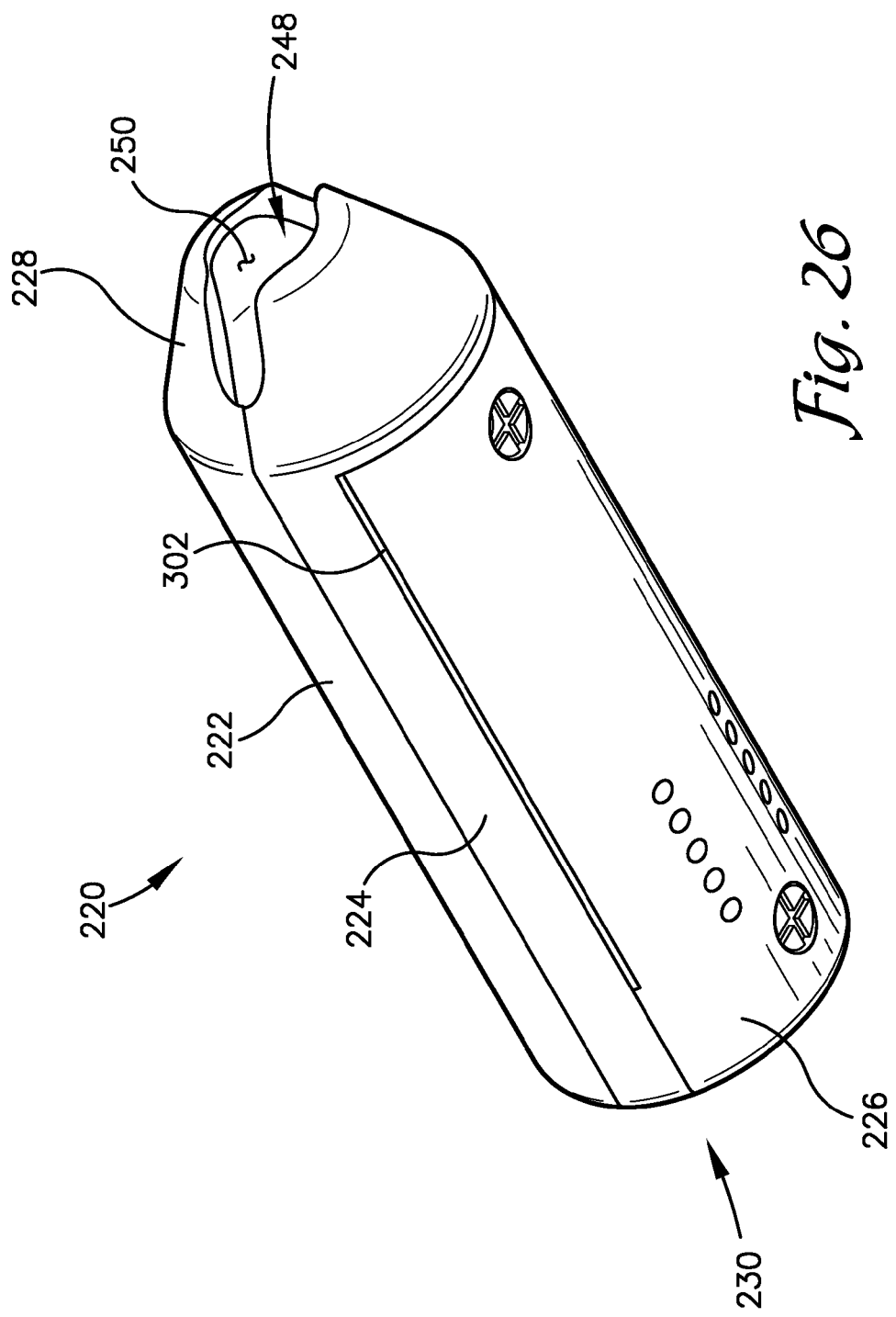
FIG. 26 is a top perspective view of an assembled sensor assembly separated from a cable assembly depicted in accordance with an embodiment of the invention.

As best seen in FIGS. 17 and 25, the intermediate portion 224 and base 222, together, form a passageway 248 therebetween with a cross-sectional profile substantially similar to that of the cable assemblies 206, 208 and configured to accept the cable assembly 206, 208 therethrough. The leading and trailing ends 228, 230 of the intermediate portion 224 and base 222 form openings 250 to the passageway 248 and have a profile that substantially matches that of the cable assembly 206, 208. An interior surface 252 of the intermediate portion 224 is configured to substantially conform to the profile of the cable assembly 206, 208 as are distal ends of the bosses 236 on the base 222.

Referring to FIGS. 19 and 21, the intermediate portion 224 includes a plurality of apertures 254 that extend from a mounting surface 256 through the thickness of the intermediate portion 224 to the interior surface 252 and align with the bosses 236 on the base 222. The apertures 254 may include counter-sink portions associated therewith and configured to accept a head of a fastener 262, e.g. a screw. The apertures 254 are each located within a respective rectangular recess 264 in the mounting surface 256. In another embodiment, the apertures 254 are flush with the mounting surface 256.

The fasteners 262 comprise zinc-plated screws or any similar fastener and are inserted through respective apertures 254, extend across the passageway 248, and engage threaded bores in the respective bosses 236 to couple the intermediate portion 224 and base 222 together. The heads of the fasteners 262 are flush with or protrude just above the mounting surface 256.

With further reference to FIG. 18, a pair of fastener enclosures 266 protrudes from near opposite ends of the mounting surface 256. Each of the enclosures 266 is configured to accept a nut 268 that is inserted from the interior surface 252. The fastener enclosures 266 retain the nut 268 and inhibit rotation thereof for coupling to a fastener 270 inserted through the cover 226 as described below. Other fasteners 270 and configurations thereof might be employed in embodiments of the invention. For example, the fastener enclosures might be threaded to enable direct coupling to the fastener 270 or a self-tapping fastener 270 might be employed.

With reference to FIGS. 19 and 22, the cover 226 mounts on the intermediate portion 224 over the mounting surface 256 and encloses the sensor device 216, 218 therebetween. An exterior surface 272 of the cover 226 completes the cylindrical form of the sensor assembly 202, 204. A pair of apertures 274 is provided through the exterior surface 272 and aligns with the pair of fastener enclosures 266 on the intermediate portion 224 such that the fasteners 270 are inserted therethrough to engage the nuts 268 and retain the cover 226 in a mounted position on the intermediate portion 224. A plurality of perforations 276 are also provided through the exterior surface 272 and are configured to enable air flow through the cover 226 but to at least partially inhibit liquid and solid particulate from passing through the cover 226.

A top and a bottom wall 278, 280 are provided at opposite ends of the cover 226 extending opposite the exterior surface 272 to enclose the ends of the cover 226. The top wall 278 is a solid wall and abuts a similar face of the intermediate portion 224 to inhibit liquid and solid particulate from entering the sensor housing 220. The bottom wall 280 includes a plurality of apertures, slots, or notches 284 that enable additional airflow through the perforations 276 and drainage of liquids and/or solids that might enter through the perforations 276.

Referring to FIGS. 23 and 24, an interior surface 286 of the cover 226 supports the sensor device 216, 218. A plurality of mounting pegs 288 extend from the interior surface 286 for receipt by respective mounting holes 290 in a circuit board 292 of the sensor devices 216, 218. Support surfaces or shoulders 294 are also formed integral with or extend from the interior surface 286 and terminate in a common plane for receipt of the circuit board 292 thereon. The common plane is recessed into the cover 226 such that a back surface 296 of the circuit board 292 is substantially flush with edges 298 of the cover 226. The edges 298 are also recessed a distance with respect to an abutting edge 300 of the cover 226 to provide a gap between the edges 298 and the mounting surface 256 of the intermediate portion 224; the abutting edge 300 abuts the mounting surface 256.

As shown in FIG. 19, a front surface 301 of the circuit board 292 is held spaced apart from the interior surface 286 of the cover 226. And a relative humidity sensor 303 disposed on the circuit board 292 of a sensor device 216 is disposed adjacent to the perforations 276 in the cover 226 for exposure to air entering the sensor housing 220. Sensor devices 218 that sense only temperature might be similarly positioned on the cover 226 but do not include a relative humidity sensor 303.

A non-conductive, closed-cell foam gasket 302 is placed on the back surface 296 of the circuit board 292. The gasket 302 might also be formed from a non-conductive rubber, silicon, or other similar material. The gasket 302 is dimensioned to extend beyond side edges of the circuit board 292 and onto the recessed edges 298 of the cover 226. The gasket 302 thereby fills the gap between the cover 226 and the mounting surface 256 of the intermediate portion 224 and restricts infiltration or ingress of liquids and solid particulates therebetween and into contact with the circuit board 292. The gasket 302 also includes an adhesive applied to a surface thereof to adhere the gasket 302 to the back surface 296 of the circuit board 292 and to the edges 298 of the cover 226, thus securing the circuit board 292 on the cover 226.

A plurality of cutouts 304 is provided within the border of the gasket 302. The cutouts each align with one or more electrical contacts 306 disposed on the back surface 296 of the circuit board 292 that also align with the recesses 264 in the intermediate portion 224. The electrical contacts 306 are offset or align with the heads of the fasteners 262 disposed in the respective recesses 264. An electrically conductive, elastomeric pad 308 is disposed in each of the recesses 264 in contact with both the heads of the fasteners 262 and the respective electrical contact 306 on circuit board 292 to provide electrical communication therebetween. The electrical contacts 306 may extend in direct contact with the fasteners 262 or with a separate electrical contact (not shown) instead of the fasteners 262. In another embodiment, the fasteners 262 and electrical contacts 306 are comprised of the same or similar materials and no pads 308 are used.

The elastomeric material of the pads 308 (see FIG. 19) is impregnated, filled, or otherwise contains nickel-plated aluminum or a similar material to provide electrical conductivity to the pad and to reduce galvanic corrosion between the dissimilar metals that comprise the fasteners 262 and the electrical contacts 306. For example, the pads 308 reduce or eliminate corrosion that might occur between a zinc-plated fastener 262 that is placed in contact with a tin-lead electrical contact 306, especially in a humid environment such as that found within the grain 11 of the grain bin 10. It is understood that the fasteners 262, electrical contacts 306, and pads 308 might be configured of different alloys and filler materials without departing from the scope of embodiments of the invention.

The elastomeric pads 308 comprise a hollow tube with a D-shaped cross-sectional shape. As such, a flat face 310 of the pad 308 is placed in contact with an electrical contact 306 on the circuit board 292. The flat face 310 might include an adhesive coating to enable the pad 308 to be affixed to the electrical contact 306. An arced portion 312 of the pad 308 has a height greater than the depth of the recess 264 such that the arced portion 312 contacts the respective fastener 262 in the recess 264 and is at least slightly compressed between the circuit board 292 and the intermediate portion 224. In another embodiment, the pads 308 might be disposed in the recesses 264 and affixed to the fasteners 262 instead of to the electrical contacts 306 or the pads 308 might be placed in contact with more than one electrical contact 306 or fastener 262. The elastomeric pads 308 might be configured in any of a variety of other forms without departing from the scope of embodiments of the invention described herein.

With continued reference to FIGS. 16-26, assembly of the sensor assemblies 202, 204 on the respective cable assembly 206, 208 is described in accordance with an embodiment of the invention. Any number and combination of the sensor assemblies 202 and 204 can be coupled to a single cable assembly 206 or 208. As described herein, only the sensor assemblies 202 that sense both relative humidity and temperature are installed on the cable assembly 206 and only the sensor assemblies 204 that sense temperature only are installed on the cable assembly 208, but embodiments of the invention are not so limited. A variety of the sensor assemblies 202 and 204 might be installed on a single cable assembly 206/208. The sensor assemblies 202, 204 can be installed at any location along the length of the respective cable assembly 206, 208. The sensor assemblies 202, 204 can also be installed at any regular or irregular interval or spacing along the length of the cable assembly 206, 208.

To install a sensor assembly 202, 204, a location along the length of the cable assembly 206, 208 for installation is determined. Initially, the sensor assembly 202, 204 is in a disassembled condition in which the base 222, intermediate portion 224, and cover 226 are separated. But the appropriate sensor device 216, 218 is installed on the cover 226, e.g. the circuit board 292 of the sensor device 216, 218 is affixed to the cover by the gasket 302. And the pads 308 are affixed to the electrical contacts 306 on the circuit board 292.

The nuts 268 are inserted into the fastener enclosures 266 in the intermediate portion. In an embodiment, the nuts 268 are integral with the intermediate portion 224, e.g. the nuts 268 are molded in place. The base 222 and the intermediate portion 224 are placed against opposite sides of the cable assembly 206, 208 to enclose the cable assembly 206, 208 within the passageway 248 and to engage the flanges 238 on the base 222 in the recesses 244 on the intermediate portion 224. The fasteners 262 are inserted through the apertures 254 in the intermediate portion 224. The fasteners 262 pierce through the casing 214 of the cable assembly 206, 208 to extend beyond the cable assembly 206, 208 to engage the bosses 236 on the base 222. The casing 214 is of sufficient resilience or hardness to form a liquid tight seal around the fasteners 262 to avoid infiltration of liquids into the casing 214 and cable assembly 206, 208. The casing 214 and the number of fasteners 262 employed also provide sufficient strength to maintain the coupling and position of the sensor assembly 202, 204 on the cable assembly 206, 208 under loads applied by grain 11 flowing along the sensor assembly 202, 204 and cable assembly 206, 208.

As each of the fasteners, or conductive piercing members 262 pierce through the casing 214, they also contact at least one of the communication wires 212 disposed therein to provide a pathway for electrical communication between the fasteners 262 and the wires 212. The fasteners 262 might partially cut into strands in the wires 212 and/or through a protective sheathing around the wires 212. The position of the wires 212 in the cable assembly 206, 208 is maintained by the casing 214 to sufficiently align with the apertures 254 and bosses 236 to enable the fasteners 262 disposed therein to contact the wires 212. The alignment might be slightly offset to avoid the fasteners 262 cutting completely through the wires 212.

In one embodiment, the cable assembly 206, 208 employs pairs of communication wires 212. The communication wires 212 of the pair are spaced apart a distance that is less than the width or diameter of the fasteners 262. The fasteners 262 pierce the cable assembly 206, 208 between the communication wires 212 of the pair and contact both wires 212 of the pair to electrically couple therewith.

Next, cover 226 is mounted on the intermediate portion 224 and secured thereto by inserting the fasteners 270 through the apertures 274 and engaging the nuts 268 contained in the fastener enclosures 266. Mounting of the cover 226 on the intermediate portion 224 places the pads 308 into the rectangular recesses 264 in the intermediate portion 224 and into contact with the heads of the respective fasteners 262. As such, the electrical contacts 306 and the sensor device 216, 218 are placed into electrical communication with the communication wires 212 via the pads 308 and the fasteners 262. As depicted in FIG. 23 six electrical contacts 306, pads 308, and fasteners 262 are employed to provide a number of redundant paths for electrical communications between the sensor device 216, 218 and the control unit 24 to which it is coupled via the wires 212. Such redundancy is intended to insure that a communication path is available even when one or more paths might be disconnected by corrosion or the like. Such might also insure that at least one of the fasteners 262 makes good contact with the wires 212, e.g. when one or more fasteners 262 fail to contact the wires 212 when piercing the casing 214 of the cable assembly 206, 208. Any number of electrical contacts 306, pads 308, and fasteners 262 can be employed in embodiments of the invention.

A desired number of additional sensor assemblies 202, 204 are subsequently installed at desired locations along the cable assembly 206, 208. The cable assembly 206, 208 is suspended in the grain bin 10 by the support cable 210 as discussed previously above and the wires 212 are coupled to the control unit 24.

The sensor assemblies 202, 204 can also be replaced, removed, or additional sensor assemblies 202, 204 added to the cable assemblies 206, 208. These changes can be made before or after installation of the cable assemblies 206, 208 in the grain bin 10, such as, for example when a sensor assembly 202, 204 or sensor device 216, 218 is damaged. To replace a sensor assembly 202, 204 with a defective or damaged sensor device 216, 218, the cover 226 with the sensor device 216, 218 affixed thereto can be replaced with another cover 226 and sensor device 216 without removing the base 222 and intermediate portion 224 from the cable assembly 206, 208. Or the defective or damaged sensor device 216, 218 might be removed from the cover 226 and another operational sensor device 216, 218 affixed thereto. If the sensor housing 220 is damaged, the base 222, intermediate portion 224, and cover 226 can be removed and the damaged component 222, 224, and/or 226 replaced or the entire housing 220 replaced.

Similarly, the sensor assemblies 202, 204 can be removed from the cable assembly 206, 208 and moved to a new location thereon by disassembling the sensor assemblies 202, 204 and reassembling at the new location. In an embodiment, the casing 214 has sufficient resilience to at least partially heal or retract to fill in any holes left in the casing 214 after removal of the fasteners 262.

It is foreseen that the base 222 and the intermediate portion 224 forming the sensor support 227 may be formed or molded as a single part with a central bore sized to receive the cable assemblies 206, 208 such that the sensor supports 227 can be slid onto the cable assemblies 206, 208. It is also foreseen that the base 222 and intermediate portion 224 may be molded as a single part and connected together by a living hinge to permit folding of the base 222 and intermediate portion 224 around a cable assembly 206, 208 to enclose the cable assembly 206, 208 therebetween. The sensor support 227 is preferably designed and formed to be sufficiently rigid to support the electronic sensor 216, 218 and prevent damage to the circuit board 292 by resisting flexing or the like.

It is also foreseen that instead of screws, the conductive piercing members could be formed as relatively sharp or pointed members without threads for piercing through the cable casing 214 and into contact with a respective communication wire 212. An opposite end or head of the conductive piercing member would remain exposed for forming a contact or pressure type, electrical connection with a respective electrical contact 306 on the sensing device 216, 218. The electrical contact between the contact 306 and head of the conductive piercing member, such as screw 262 may be indirect, as in the embodiment shown using a resilient pad 308, or the contact may be a direct contact. It is also foreseen that the contact 306 could include a conductive pin or the like received in a conductive receiver formed in the conductive piercing member or an intermediate electrical conductor between the contact 306 and the conductive piercing member. In a preferred embodiment, such as the embodiment shown in FIGS. 16-26, electrical contact between the communication wires 212 and the contacts 306 on the electronic sensor 216, 218 is made upon securing the cover 226 and attached electronic sensor 216, 218 to the sensor support 227.

Operation

As generally shown in FIG. 2, the cable assemblies 28, 30, 206, 208 with sensor assemblies 40, 42, 202, 204 mounted thereon are suspended from the ceiling of the bin 10 and extend toward the floor 15 prior to filling the bin 10 with grain 11. The bin 10 is then filled with grain 11 so that the cable assemblies 28, 30, 206, 208 with sensor assemblies 40, 42, 202, 204 mounted thereon extend into the mass of the stored grain 11. Air voids are formed between the individual seeds or grains 11, and it is the relative humidity and temperature of the air in the voids that is measured by the sensor assemblies 40, 42, 202, 204 to determine the moisture content of the grain 11.

As seen in FIGS. 2 and 11, the plenum sensor assembly 32 is mounted in and extends through the sidewall 12 of the grain bin 10 into the plenum chamber 14. The plenum sensor assembly 32 includes a breathable plastic tube 116 with both relative humidity and temperature sensors 118 and 120 mounted therein to measure the temperature and the moisture content of the air being pushed into the grain 11 by the fan 16. The plenum sensor assembly 32 also includes an air pressure tube 122 for conducting the air pressure within the plenum chamber 14 to the distributed control unit 25 where it is measured. This allows the system to determine if the fan 16 is running. Also, if the grain 11 within the bin 10 is very wet, the air pressure increases.

The weather station 34 is shown in FIGS. 1, 2, and 12. The weather station 34 includes a pair of sensor boards (not shown) for measuring the relative humidity and air temperature outside the grain bin 10. The sensor boards are mounted within a breathable plastic tube 130 and a vented radiation shield 132 to protect them from the environment. Preferably, the weather station 34 is colored white to reflect the sun's rays and is mounted to the exterior sidewall 12 of the grain bin 10 away from the fan 16 to obtain the most accurate readings.

It is most preferable for the system 20 to include both the plenum sensor 32 and the weather station 34 as described to obtain the most accurate measurements for optimum drying. For instance, the measurements taken by the plenum sensor 32 and the weather station 34 may differ given the heat added to the air in the plenum chamber 14 as a result of the air movement through the fan 16, the increased pressure in the plenum chamber 14 and the heat given up or absorbed by the ground that forms nearly half of the plenum chamber 14 surface area. However, one weather station 34 may be adequate for a cluster 21 of nearby bins 10.

The cellular modem or low power local radio 36 is preferably mounted on the bin's roof 13 for the most effective signal transmission. If a cellular modem 36 is included, then its antenna 134 is mounted nearby. As shown in FIG. 2, the antenna 134 is mounted on the roof 13 of the grain bin 10. For cost savings, one cellular modem 36 and weather station 34 may be shared among a cluster 21 of bins 10, with each of the other systems 20 on nearby bins 10 using a low power radio 36, to provide the local communication between the bins 10 and the cellular modem providing the remote communication from the cluster 21.

Figure 4:
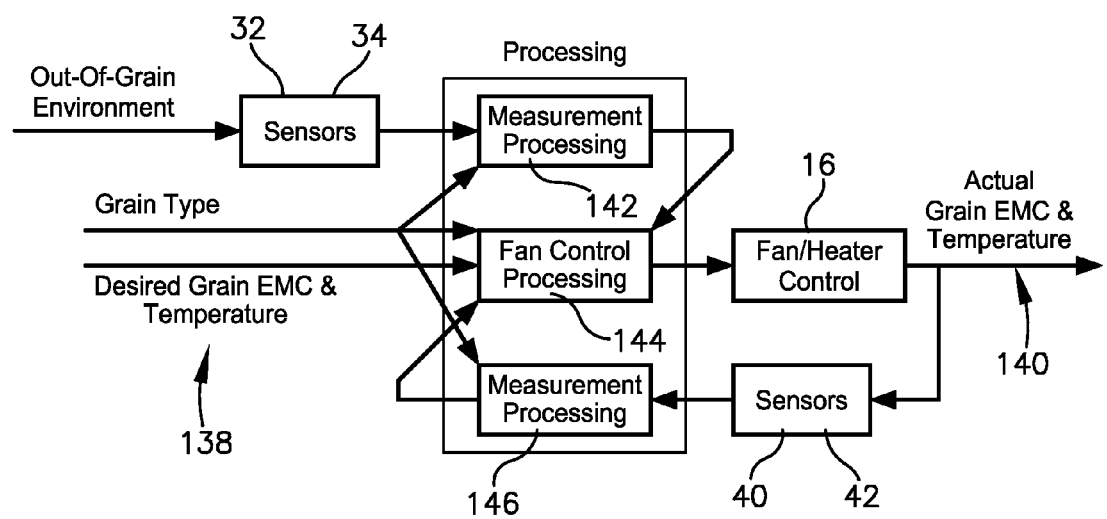
FIG. 4 is a flow chart showing the grain drying system's control processing in accordance with an embodiment of the invention.

The master control unit 22 controls the operation of the bin's fan 16 (and heater, if installed) using the closed loop control system shown in FIG. 4. The system's input 138 is the grain type and the desired or selected EMC and temperature. These are entered by the user at the master control unit 22 or through the remote user interface or computer 38. These settings 138 may be determined and set once per season or updated frequently. The settings 138 are stored in the master control unit's non-volatile memory 52 so that the system 20 can operate without continual intervention or even a connection to a user or outside computer. The system's output 140 is the actual EMC and temperature.

The sensor processing 142 and 146 is partially performed in the distributed control units 24 and 25 before being passed to the master control unit 22 for completion. The distances between the sensor assemblies 32, 34, 40, 42, 204, 206 and the distributed control units 24 and 25 are made relatively short to reduce the susceptibility of the electrical signals between them to electromagnetic interference. Accordingly, in the preferred embodiment, some of the sensor processing is done at the distributed control units 24 and 25 which are mounted around the exterior of the grain bin 10 in relatively close proximity to the sensor assemblies 32, 34, 40, 42, 204, 206. That part of the sensor processing 142 and 146 that is done in distributed control units 24 and 25 might be to verify the integrity of the sensor data, to perform averaging, and to convert it to a form that can be used by the master control unit 22.

The cable assemblies 28, 30, 206, 208 are powered by the distributed control unit 24 one at a time. The control unit 24 sends commands to the circuit board 84, 85 or sensor device 216, 218 on the powered cable 28, 30, 206, 208 by switching off and on the power on that cable 28, 30, 206, 208. Switching between the two states, on and off, provides the digital communication. Each circuit board 84, 85 or sensor device 216, 218 contains an address that is also a relative location of the circuit board 84, 85 or sensor device 216, 218 on the cable assembly 28, 30, 206, 208. For example, the circuit board 84, 85 or sensor device 216, 218 farthest from the distributed control unit 24 has an address of "1". The circuit board 84, 85 or sensor device 216, 218 next closest to the distributed control unit 24 has an address of "2" and so on. The addresses differentiate one circuit board 84, 85 or sensor device 216, 218 from another on the same cable assembly 28, 30, 206, 208.

The messages communicated from the distributed control unit 24 to the sensors 86, 87, 216, 218 are called commands and every command contains the address of the destination sensor 86, 87, 216, 218. Every message from circuit board 84, 85, or sensor device 216, 218 to the distributed control unit 24 is a response, and every response contains the source address of the circuit board 84, 85 or sensor device 216, 218. The circuit board 84, 85 or sensor device 216, 218 creates a response by switching a load on and off while the distributed control unit 24 has the voltage at its high level. Thus, the current changes between a low current and a high current and is detected by a current circuit of the distributed control unit 24.

When the distributed control unit 24 is not communicating with a particular string of sensor assemblies 40, 42, 202, 204 on a cable assembly 28, 30, 206, 208, it leaves the power off on that cable 28, 30, 206, 208. Thus, the sensors' microprocessors are reset each time the power is applied before another measurement and communication event. While the distributed control unit 24 transmits by switching power off for brief periods, capacitors on the sensor circuit boards 84, 85, 292 keep the sensors' circuitry active.

Both local communication between systems 20 on nearby bins 10 and remote communication with a remote user interface 38 are coordinated through the distributed control unit 26. This distributed control unit 26 communicates with the system's low power local radio or cellular modem 36.

Remote communication includes communication from the system 20 to the remote user interface 38 as well as communication from the remote user interface 38 to the system 20. For instance, daily status reports containing the hourly temperature and moisture content, the time the fan 16 has operated and other data that is of interest to a user who may be monitoring system performance is transmitted from the system 20. Remote communication also includes the transmission of alarm conditions, which can be displayed through the browser and/or communicated to the user via text message, telephone or e-mail. Lastly, remote communication includes incoming messages from the remote user interface 38 for purposes of changing system inputs 138, such as the grain or commodity type, desired temperature and desired EMC.

Local communication includes collecting and distributing remote communication when only one cell modem 36 is installed in a cluster 21 of nearby bins 10. It also includes the distribution of information from the weather station 34 when one weather station 34 is installed in a cluster 21 of bins 10.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. A grain-bin monitoring system comprising:
    a cable including a support member, a first conductor, and a second conductor, the support member and the first and second conductors extending along a longitudinal axis of the cable and being encased in a casing that maintains relative cross-sectional positions of the support member and the first and second conductors along the cable; and
    a sensor assembly removably securable to the cable and comprising a sensor housing, the sensor housing comprising a base, an intermediate portion, and a cover, the base being configured to be coupled to the intermediate portion by first and second fasteners to interpose the cable therebetween to allow the first and second conductors to pass continuously through the sensor assembly, the first fastener extensible into the casing to contact the first conductor, the second fastener extensible into the casing to contact the second conductor, the cover being configured to be coupled to the intermediate portion to interpose a sensor device therebetween, the sensor device including first and second electrical contacts configured to be in electrical communication with the first and second fasteners, respectively, when the cover is coupled to the intermediate portion.

2. The grain-bin monitoring system of claim 1, further comprising:
    a third conductor disposed adjacent to the first conductor to form a first pair;
    a fourth conductor disposed adjacent to the second conductor to form a second pair, and
    wherein when the sensor assembly is coupled to the cable, the first fastener extends into the cable between the first and third conductors and the second fastener extends into the cable between the second and fourth conductors.

3. The grain-bin monitoring system of claim 1, further comprising an electrically conductive elastomeric pad disposed between each of the first and second fasteners and the first and second contacts, respectively, to electrically connect the first and second electrical contacts with the first and second fasteners, respectively.

4. The grain-bin monitoring system of claim 1, wherein the sensor housing comprises a cylindrical body having a frusto-conical end portion that tapers inward and upward in an installed position to reduce drag forces on the sensor assembly, when positioned in a grain bin, due to grain particulate flowing past the sensor assembly.

5. The grain-bin monitoring system of claim 1, wherein the sensor device measures one or more of relative humidity or temperature.

6. A grain-bin monitoring system comprising:
    a cable configured to be suspended in a quantity of grain in a grain bin, the cable including a support member and at least two communication members extending along a longitudinal axis of the cable, the cable including a flexible casing configured to maintain relative cross-sectional positions of the support member and the communication members; and
    first and second sensor assemblies, each being removably couplable to the cable and comprising a sensor device having at least two electrical contacts, wherein when coupled to the cable, the communication members extend continuously along and beyond the first and second sensor assemblies to permit each of the electrical contacts to be in electrical communication with the communications members via respective coupling members that extend into the flexible casing of the cable and contact a respective one of the communication members,
    wherein the first and second sensor assemblies each comprise a central channel extending therethrough, and wherein when the first and second sensor assemblies are coupled to the cable, the cable extends through the first and second sensor assemblies within the central channels thereof.

7. The grain-bin monitoring system of claim 6, wherein each sensor device includes a plurality of redundant electrical contacts and respective coupling members.

8. The grain-bin monitoring system of claim 6, wherein the cable includes four communication members that are grouped into first and second pairs of communication members, and wherein each of the coupling members extend into the flexible casing of the cable between the communication members of the first or second pairs, the coupling members each having a width that is larger than a space between the communication members in the first and second pairs to permit each of the coupling members to contact both of the communication members of the respective pair.

9. The grain-bin monitoring system of claim 6, wherein the first and second sensor assemblies each comprises a housing, each housing comprising:
   a base;
   an intermediate portion coupled to the base, the intermediate portion and the base forming a passageway therebetween that is configured to accept the cable therein, the coupling members comprising fasteners that couple the intermediate portion to the base with the cable interposed therebetween; and
   a cover coupled to the intermediate portion opposite the base, the sensor device being disposed between the intermediate portion and the cover.

10. The grain-bin monitoring system of claim 6, wherein each sensor device measures one or more of relative humidity or temperature.

11. A condition sensing cable assembly for sensing conditions in a grain bin, the assembly comprising:
   a cable having a longitudinal axis and including first and second conductors extending along the axis, the first and second conductors encased in a cable casing that maintains relative cross-sectional positions of the first and second conductors along the cable;
   a sensor assembly securable to the cable, the sensor assembly including (i) an electronic sensor having first and second electrical contacts and (ii) a sensor housing comprising a sensor support and a cover, the sensor support coupled the cable to allow the first and second conductors to pass continuously through the sensor assembly, the cover configured to enclose the electronic sensor within the sensor assembly when fastened to the sensor support; and
   first and second conductive members, the first conductive member extending into the cable casing and extending in electrical contact with the first conductor, the second conductive member extending into the cable casing and extending in electrical contact with the second conductor;
   wherein the electronic sensor is supported against the sensor support with the first and second electrical contacts in electrical communication with the first and second conductive members, respectively.

12. The cable assembly of claim 11, wherein the electrical communication between the first and second electrical contacts of the electronic sensor and the first and second conductive members is maintained by pressure contact.

13. The cable assembly of claim 12, further comprising an electrically conductive elastomeric pad disposed between each of the first and second conductive members and the first and second contacts.

14. The cable assembly of claim 11, wherein the sensor housing comprises a cylindrical body having a frusto-conical end portion that tapers inward and upward in an installed position to reduce drag forces on the sensor assembly, when positioned in a grain bin, due to grain particulate flowing past the sensor assembly.

15. The cable assembly of claim 11, wherein the electronic sensor measures one or more of relative humidity or temperature.

16. The cable assembly of claim 11, wherein the electronic sensor is mounted on the cover, and the cover is removably securable to the sensor support.

17. The cable assembly of claim 11, wherein the cable further comprises a support member extending along the longitudinal axis of the cable in parallel with respect to the first and second conductors.

18. The cable assembly of claim 11, wherein the electronic sensor comprises a circuit board, and the sensor support comprises a rigid material to resist flexing of the circuit board.

19. The cable assembly of claim 11, wherein the sensor housing comprises openings formed therein to allow the electronic sensor to be exposed to ambient air when positioned within a grain bin to sense a condition in the grain bin.

20. The cable assembly of claim 11, further comprising first and second electrically conductive components disposed between the first and second conductive members and the first and second contacts, respectively.

21. The cable assembly of claim 11, wherein the sensor assembly comprises a central channel extending therethrough, and wherein when the sensor assembly is coupled to the cable, the cable extends through the sensor assembly within the central channel thereof.

\* \* \* \* \*